(12) United States Patent
Chen et al.

(10) Patent No.: US 7,208,278 B2
(45) Date of Patent: Apr. 24, 2007

(54) CONCATAMERIC LIGATION PRODUCTS: COMPOSITIONS, METHODS AND KITS FOR SAME

(75) Inventors: Caifu Chen, Palo Alto, CA (US);
Kevin Hennessy, San Mateo, CA (US);
Kai Qin Lao, Pleasanton, CA (US);
Teodoro Paner, Dublin, CA (US);
Vinod Mirchandani, San Ramon, CA (US)

(73) Assignee: Applera Corporation, Foster City, CA (US)

( * ) Notice: Subject to any disclaimer, the term of this patent is extended or adjusted under 35 U.S.C. 154(b) by 57 days.

(21) Appl. No.: 10/982,619

(22) Filed: Nov. 4, 2004

(65) Prior Publication Data

US 2006/0063163 A1    Mar. 23, 2006

Related U.S. Application Data

(60) Provisional application No. 60/517,470, filed on Nov. 4, 2003.

(51) Int. Cl.
*C12Q 1/68* (2006.01)
*C12P 19/34* (2006.01)
*C07H 21/04* (2006.01)

(52) U.S. Cl. ................. 435/6; 435/91.2; 536/24.2

(58) Field of Classification Search ............... None
See application file for complete search history.

(56) References Cited

U.S. PATENT DOCUMENTS

2002/0076704 A1* 6/2002 Weissman et al. ............ 435/6
2003/0108902 A1   6/2003 Abarzua

OTHER PUBLICATIONS

Grossman et al., High-density multiplex detection of nucleic acid sequences; oligonucleotide ligation assay and sequence-coded separation, Nucleic Acids Res. (1994) 22: 4527-4534.*

H. Yamakawa et al., "Properties and Anti-HIV Activity of Nicked Dumbbell Oligonucleotides" Nucleosides & Nucleotides, vol. 15 (1-3), 1996, pp. 519-529.

H. Gamper et al., "Evidence for A Four-Strand Exchange Catalyzed by the RecA Protein" Biochemistry, vol. 39, Jul. 2000, pp. 15272-15281.

K. Hosono et al., "Properties and Anti-HIV Activity of Hairpin Antisense Oligonucleotides Containing 2'-Methoxynucleosides with Base-Pairing in the Stem Region at the 3'-End" Antiviral Chemistry & Chemotherapy, vol. 7, (2), 1996, pp. 86-93.

A. Okamoto et al., "P-Loop Catalytically Assisting the Enzymatic Cleavage of Single-Stranded DNA" Bioorganic & Medicinal Chemistry, vol. 11, Mar. 2003, pp. 3747-3751.

International Search Report mailed Apr. 19, 2005 issued in International Application No. PCT/US2004/037284.

* cited by examiner

*Primary Examiner*—Jeffrey Fredman
*Assistant Examiner*—David C. Thomas
(74) *Attorney, Agent, or Firm*—Andrew K. Finn

(57) ABSTRACT

The present teachings relate to methods, compositions, and kits for detecting one or more target polynucleotide sequences in a sample, and methods compositions and kits for forming concatameric ligation products. In some embodiments of the present teachings, oligonucleotides are hybridized to complementary target polynucleotides and are ligated together to form a concatameric ligation product. In some embodiments of the present teachings, the concatameric ligation product can be amplified, and the identity and quantity of the target polynucleotides determined based on sequence introduced in the ligation reaction. Some embodiments of the present teachings provide methods for removing unligated probes from the reaction mixture. Some embodiments of the present teachings provide for highly multiplexed detection, identification, and quantification of a plurality of target polynucleotides using a variety of analytical procedures.

6 Claims, 7 Drawing Sheets

Legend

— Universal PCR primer sequence
— Universal reverse PCR priming site
— Genome equivalent region
–ww– ZipCode sequence
⟨ Oligo
⎯⟩⎯⎯⎯ Spacer
Ⓟ 5' phosphate
LSO Locus-specific oligo
ASO$_{A1}$ Allele-specific oligo A1
ASO$_{A2}$ Allele-specific oligo A2
ASO$_{L1}$ ASO linker L1
ASO$_{L2}$ ASO linker L2
—Ⓓ Universal reverse PCR primer, biotinylated
— Universal forward PCR primer ZipChute probe:
∗—— Fluorescent dye label
⎯/⌐⎯ Mobility modifiers
⎯⎯⎯ ZipCode sequence
⎯ww⎯Y SNPlex Hybridization Plate

FIG. 9G

CONCATAMERIC LIGATION PRODUCTS: COMPOSITIONS, METHODS AND KITS FOR SAME

RELATED APPLICATIONS

This application claims priority to U.S. Provisional Application No. 60/517,470, filed Nov. 4, 2003, for "Polynucleotide Detection by Linear and Looped Concatameric Ligation Assay" by Chen et al, the entire contents of which is incorporated herein by reference.

FIELD

The present teachings relate to methods, compositions, and kits for forming concatameric ligation products, and for detecting one or more target polynucleotide sequences in a sample.

INTRODUCTION

Numerous fields in molecular biology require the identification of target polynucleotide sequences. Hybridization and ligation are two frequently used procedures employed to query the identity of target polynucleotides. The increasing amount of sequence information available to scientists in the post-genomics era has produced an increased need for rapid, reliable, low-cost, high-throughput, sensitive, and accurate methods to query complex nucleic acid samples.

SUMMARY

Some embodiments of the present teachings provide a method of forming a concatameric ligation product comprising; providing a target polynucleotide, a primary looped linker, a primary oligonucleotide, a secondary oligonucleotide, and a secondary looped linker; performing, in any suitable order: hybridizing the primary oligonucleotide and the secondary oligonucleotide to the target polynucleotide; hybridizing the primary looped linker to the primary oligonucleotide; hybridizing the secondary looped linker to the secondary oligonucletide; ligating the primary looped linker to the primary oligonucleotide; ligating the primary oligonucleotide to the secondary oligonucleotide; and, ligating the secondary oligonucleotide to the secondary looped linker; and, forming a concatameric ligation product.

Some embodiments of the present teachings provide a method of forming a nuclease-resistant ligation product comprising; providing a target polynucleotide, a primary looped linker, a primary oligonucleotide, a secondary oligonucleotide, and a secondary looped linker, wherein the primary looped linker comprises a blocking moiety, the secondary looped linker comprise a blocking moiety, or the primary looped linker comprises a blocking moiety and the secondary looped linker comprises a blocking moiety; performing, in any suitable order; hybridizing the primary oligonucleotide and the secondary oligonucleotide to the target polynucleotide; hybridizing the primary looped linker to the primary oligonucleotide; hybridizing the secondary looped linker to the secondary oligonucleotide; ligating the primary looped linker to the primary oligonucleotide; ligating the primary oligonucleotide to the secondary oligonucleotide; and, ligating the secondary oligonucleotide to the secondary looped linker; thereby forming a nuclease-resistant ligation product; and; optionally treating the nuclease-resistant ligation product with at least one nuclease wherein the nuclease resistant ligation product internal to the blocking moiety(s) is not degraded by the nuclease.

Some embodiments of the present teachings provide a method of determining a target polynucleotide comprising; forming a concacatmeric ligation product, wherein the concatameric ligation product comprises a primary looped linker, a primary oligonucleotide, a secondary oligonucleotide, and a secondary looped linker; measuring the concatameric ligation product; and, determining the target polynucleotide.

Some embodiments of the present teachings provide a method of determining an allele at a single nucleotide polymorphism (SNP) locus comprising; forming a concatameric ligation product, wherein the concatameric ligation product comprises a primary looped linker, a primary oligonucleotide, a secondary oligonucleotide, and a secondary looped linker, wherein the primary oligonucleotide comprises a 3' discriminating nucleotide, measuring the concatameric ligation product; and, determining the identity of the allele at the SNP locus.

Some embodiments of the present teachings provide a step of ligating, a step of nuclease-mediated digesting, a step of amplifying, a step of detecting, or combinations thereof.

The present teachings also provide compositions and kits for performing the described methods.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF EXEMPLARY EMBODIMENTS

Figure 1:
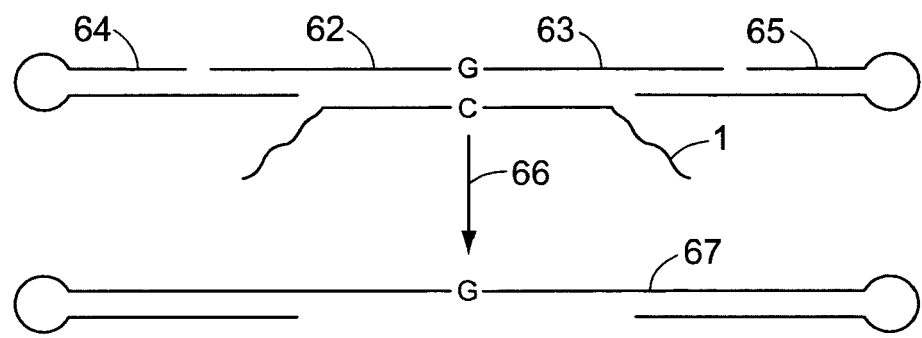
FIG. 1 depicts certain aspects of various compositions according to some embodiments of the present teachings.

Aspects of the present teachings may be further understood in light of the following exemplary embodiments, which should not be construed as limiting the scope of the present teachings in any way. The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Definitions

As used herein, the term "target polynucleotide" refers to a polynucleotide sequence that is sought to be detected. The target polynucleotide can be obtained from any source, and can comprise any number of different compositional components. For example, the target can be nucleic acid (e.g. DNA or RNA), transfer RNA, siRNA, mRNA, various non-coding RNAs, and can comprise nucleic acid analogs or other nucleic acid mimic. The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809, the Flexigene kit (Qiagen), the Paragene kit (Gentra), and the mirVana RNA isolation kit (Ambion), etc. It will be appreciated that target polynucleotides can be cut or sheared prior to analysis, including the use of such procedures as mechanical force, sonication, restriction endonuclease cleavage, heat, or any method known in the art. In general, the target polynucleotides of the present teachings will be single stranded, though in some embodiments the target polynucleotide can be double stranded, and a single strand can result from denaturation. It will be appreciated that either strand of a double-stranded molecule can serve as the target polynucleotide.

As used herein, the term "target-specific portion" refers to the single stranded portion of an oligonucleotide that is complementary to a target polynucleotide.

As used herein, the term "allele specific oligo" or, "ASO," refers to a primary oligonucleotide that further comprises a target specific portion and a target-identifying portion, which can query the identity of an allele at a SNP locus. The target specific portion of the ASO of a primary group can hybridize adjacent to the target specific portion of the LSO of a secondary group, such that the two adjacently hybridized oligonucleotides can be ligated together. While some of the examples in the present teachings use ASO in the context of SNP determination for ease of illustration, it will be appreciated that the primary oligonucleotides can be applied in other embodiments including but not limited to gene expression analyses, methylation detection, and any other area in which target polynucleotide sequences are to be determined.

As used herein, the term "locus specific oligo" or, "LSO," refers to a secondary oligoucleotide that further comprises a target specific portion and a primer portion. The target specific portion of the LSO of a secondary group can hybridize adjacent to the target specific portion of the ASO of the primary group, such that the two adjacently hybridized oligonucleotides can be ligated together. While some of the examples in the present teachings use LSO in the context of SNP determination for ease of illustration, but it will be appreciated that the secondary oligonucleotides can be applied in other embodiments including but not limited to gene expression analyses, methylation detection, and other areas in which target polynucleotide sequences are to be determined.

As used herein, the terms "primary oligonucleotide" and "secondary oligonucleotide" refer to the two oligonucleotides that, when hybridized to adjacent regions on a target polynucleotide, can be ligated together to form a principal ligation product. For convenience of illustration, the primary oligonucleotide is depicted in the present teachings as upstream (on the 5' side of) the secondary oligonucleotide. It will be appreciated that this depiction is not limiting. Further, for convenience of illustration, the primary oligonucleotide in some embodiments is shown comprising a discriminating nucleotide on the 3' terminal of its target specific portion, but it will be appreciated that the discriminating nucleotide can be on either oligonucleotide, and further that the present teachings contemplate embodiments in which the discriminating nucleotide is located elsewhere from the 3' terminal. In embodiments where a SNP is queried, it can be convenient to consider the primary oligonucleotide as an ASO and the secondary oligonucleotide as an LSO.

As used herein, the term "non-target specific portion" refers to a portion of a primary and secondary oligonucleotide, some or all of which is substantially complementary to a splint-acting portion of an oligonucleotide so as to allow hybridization and ligation between adjacently hybridizing oligonucleotides.

As used herein, the term "primer portion" refers to a portion of an oligonucleotide, a looped linker, or both, that can serve as the substrate for the hybridization of a primer sequence. It will further be appreciated that the term "primer portion" can refer to a portion to an oligonucleotide, a looped linker, or both, the complement of which can serve as the substrate for the hybridization of a primer sequence.

As used herein, the term "primary splint linker" refers to a single stranded oligonucleotide that comprises sequence that is substantially complementary to a primary oligonucleotide and a primary distal oligonucleotide, thereby allowing for the adjacent hybridization of the primary oligonucleotide and the primary distal oliogonucleotide for their subsequent ligation.

As used herein, the term "secondary splint linker" refers to a single stranded oligonucleotide that comprises sequence that is substantially complementary to a secondary oligonucleotide and a secondary distal oligonucleotide, thereby allowing for the adjacent hybridization of the secondary oligonucleotide and the seconday distal oligonucleotide for their subsequent ligation.

As used herein the term "primary looped linker" refers to an oligonucleotdie comprising a self-complementary portion, a loop, and a single-stranded portion. As an example, an "ASO looped linker" refers to a primary looped linker comprising a PCR forward priming portion, a blocking moiety, and a single stranded portion. The single stranded portion of an ASO looped linker can hybridize with a region of the target-identifying portion of the ASO, thereby allowing ligation of the ASO looped linker to the ASO. For illustrative purposes, when depicted herein the blocking moiety is shown residing in the loop, though it will be appreciated that the present teachings contemplate embodiments in which the blocking moiety is located elsewhere. In some embodiments, especially those involving multiplexed analysis, the 3' nucleotide in a plurality of primary looped linkers is the same, which can minimize variation in ligation efficiency to the plurality of primary oligonucleotides.

As used herein the term "secondary looped linker" refers to an oligonucleotide comprising a self-complementary portion, a loop, and a single-stranded portion. As an example, an "LSO looped linker" refers to a secondary looped linker comprising a PCR reverse priming portion, a blocking moiety, and a single stranded portion. The single stranded portion of an LSO looped linker can hybridize with a region of the non-target specific portion of the LSO, thereby allowing ligation of the LSO looped linker to the LSO.

As used herein, the term "primary distal linker" refers to a single stranded oligonucleotide that comprises sequence complementary to a primary splint linker, and can hybridize adjacent to the non-target specific portion of a primary oligonucleotide on the primary splint linker, such that the primary distal linker and primary oligonucleotide can be ligated together.

As used herein, the term "primary splint linker" refers to a single-stranded oligonucleotide on which a primary distal linker and a non-target specific portion of a primary oligonucleotide can hybridize and be ligated together.

As used herein, the term "secondary distal linker" refers to a single stranded oligonucleotide that comprises sequence complementary to a secondary splint linker, and can hybridize adjacent to the non-target specific portion of a secondary oligonucleotide on the secondary splint linker, such that the secondary distal linker and secondary oligonucleotide can be ligated together.

As used herein, the term "secondary splint linker" refers to a single-stranded oligonucleotide on which a secondary distal linker and non-target specific portion of a secondary oligonucleotide can hybridize and be ligated together.

As used herein, the term "adjacent" refers to two oligonucleotides hybridizing on a complementary nucleotide sequence in a position such that their 5' and 3' termini are abutting and capable of being ligated together. As used herein, the term adjacent shall further include nearly adjacent hybridization of two oligonucleotides in such a fashion that a transient nucleotide gap can be filled in to produce abutting termini capable of being ligated together. Further, the term adjacent shall also include hybridization of oligonucleotides to form flap structures, the cleaveage of which allows abutting termini to be ligated together.

As used herein, the term "concatenated ligation product" refers to a nucleotide sequence comprising a primary looped linker or a primary distal linker, a primary oligonucleotide, a secondary oligonucleotide, and a secondary looped linker or a secondary distal linker. An example of a concatentated ligation product includes a primary distal linker ligated to an ASO, the ASO ligated to an LSO, and the LSO ligated to a secondary looped linker. Another example of a concatenated ligation product includes a primary looped linker ligated to an ASO, the ASO ligated to an LSO, and the LSO ligated to a secondary distal linker. Another example of a concatenated ligation product includes a primary looped linker ligated to an ASO, the ASO ligated to an LSO, and the LSO ligated to a secondary looped linker.

As used herein, the term "nuclease-resistant ligation product" refers to a polynucleotide comprising a primary looped linker or a primary distal linker, a primary oligonucleotide, a secondary oligonucleotide, a secondary looped linker or a secondary distal linker, and a blocking moiety. An example of a nuclease-resistant ligation product product includes a primary distal linker ligated to an ASO wherein the primary distal linker compises a blocking moiety, the ASO ligated to an LSO, and the LSO ligated to a secondary looped linker, wherein the secondary looped linker comprises a blocking moiety. Another example of a nuclease-resistant ligation product includes a primary looped linker ligated to an ASO, wherein the primary looped linker comprises a blocking moiety, the ASO ligated to an LSO, and the LSO ligated to a secondary distal linker, wherein the secondary distal linker comprises a blocking moiety. Another example of a concatenated ligation product includes a primary looped linker ligated to an ASO wherein the primary looped linker comprises a blocking moiety, the ASO ligated to an LSO, and the LSO ligated to a secondary looped linker, wherein the secondary looped linker comprises a blocking moiety. It will be appreciated that other combinations of primary oligonucleotides, secondary oligonucleotides, primary looped linkers, secondary looped linkers, primary distal linkesr, secondary distal linkers, and the presence of blocking moiety(s) are within the scope of the present teachings as well. In some embodiments, a nuclease-resistant ligation product can comprises a single blocking moiety. The term nuclease-resistant ligation product can refer both to a ligation product that has been treated with a nuclease, as well as a ligation product that has not been nuclease treated and may comprise nuclease-sensitive nucleotides external to a blocking moiety.

As used herein, the term "principal ligation product" refers to a nucleotide sequence comprising a primary oligonucleotide ligated to a secondary oligonucleotide.

As used herein, the term "blocking moiety" refers to a chemical moiety that is incorporated into an oligonucleotide and that can confer resistance to a nuclease enzyme. Exemplary blocking moieties include polyethylene glycol (PEG), C18 (18-atom hexa-ethyleneglycol) and tetra methoxyl uracil.

As used herein, the term "nuclease digestion" refers to a process whereby an enzyme can degrade an oligonucleotide.

As used herein, the term "3'-acting" nuclease refers to an enzyme that degrades oligonucleotides by commencing digestion at or near the 3' end.

As used herein, the term "5'-acting" nuclease refers to an enzyme that degrades oligonucleotides by commencing digestion at or near the 5' end.

As used herein, the term "label" refers to any moiety that, when attached to a nucleotide or polynucleotide, renders such nucleotide or polynucleotide detectable using known detection methods. Labels may be direct labels which themselves are detectable or indirect labels which are detectable in combination with other agents. Exemplary direct labels include but are not limited to fluorophores, chromophores, radioisotopes (e.g., $^{32}P$, $^{35}S$, $^3H$), spin-labels, Quantum Dots, chemiluminescent labels, and the like. Exemplary indirect labels include enzymes that catalyze a signal-producing event, and ligands such as an antigen or biotin that can bind specifically with high affinity to a detectable anti-ligand, such as a labeled antibody or avidin. Many comprehensive reviews of methodologies for labeling DNA provide guidance applicable to the present invention. Such reviews include Matthews et al. (1988); Haugland (1992), Keller and Manak (1993); Eckstein (1991); Kricka (1992), and the like. Also see U.S. Pat. Nos. 5,654,419, 5,707,804, 5,688,648, 6,028,190, 5,869,255, 6,177,247, 6,544,744, 5,728,528, and U.S. patent application Ser. No. 10/288,104.

As used herein, the term "mobility modifier" refers to a polymer chain that imparts to an oligonucleotide an electrophoretic mobility in a sieving or non-sieving matrix that is distinctive relative to the electrophoretic mobilities of the other polymer chains in a mixture.

As used herein, the term "mobility dependent analysis technique" (or MDAT) refers to an analytical technique based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like.

As used herein, the term "mobility probe" refers to an oligonucleotide binding polymer having a specific sequence of subunits designed for base-specific binding of the polymer to the target-identifying portion of the concatameric ligation product under selected binding conditions, and attached to the binding polymer, a polymer chain that imparts to an oligonucleotide an electrophoretic mobility in a sieving or non-sieving matrix that is distinctive relative to the electrophoretic mobilities of the other mobility probe(s) in said mixture. The mobility probe can further comprise a label.

As used herein, the term "primary group" refers to a collection of primary oligonucleotides, primary looped linkers, primary distal linkers, primary splint linkers, or combinations thereof.

As used herein, the term "secondary group" refers to a collection of secondary oligonucleotides, secondary looped linkers, secondary distal linkers, secondary splint linkers, or combinations thereof.

As used herein, the term "discriminating region" refers to a region on a target polynucleotide sequence that differs from another target polynucleotide region, and is the region that is of inquiry in a particular ligation reaction. Exemplary discriminating regions include but are not limited to a SNP, or a nucleotide or nucleotides that distinguish splice variants of an expressed gene, or a nucleotide that has been converted in a DNA treatment step to convert methylated cytosines in thymine.

As used herein, the term "discriminating nucleotide" refers to a discriminating region comprising a single potentially variant nucleotide.

As used herein, the term "variable oligonucleotide set" refers a plurality of primary oligonucleotides, a plurality of secondary oligonucleotides, or both that comprise target specific portions, and potentially target-identifying portions and primer portions, and that can vary according to the target polynucleotide sequences of interest in a given sample.

As used herein, the term "fixed oligonuceotide set" refers to a plurality of looped linker oligonucleotides, distal linker oligonucleotides, splint linker oligonucleotides, or combinations thereof, a finite number of which can be used to query an infinite number of target polynucleotide sequences in conjunction with a variable oligonucleotide set.

As used herein the term "sample preparation" refers to the preparation of genomic SNPs, expressed mRNA, micro RNAs, small interfering RNAs, methylated DNA, pathogen DNA, and other sources of target polynucleotide sequences, and comprises activities such as shearing, cDNA synthesis, whole genome amplification, and various related procedures that result in nucleic acids that are suitable to undergo the methods of the present teachings.

As used herein the term "internal to the blocking moiety" refers to those regions of a nuclease-resistant ligation product that are protected from nuclease degradation.

As used herein the term "external to the blocking moiety" refers to those regions of a nuclease-resistant ligation product that are sensitive to nuclease degradation.

As used herein, the term "target-identifying portion" refers to sequence on an oligonucleotide that can serve to identity the target polynucleotide. It will be appreciated that the term "target-identifying portion" can further refer to a portion of nucleic acid on an oligonucleotide, the complement of which, can serve to identify the target polynucleotide. Further, the term "target-identifying portion" refers to a moiety or moieties that can be used to identify a particular target polynucleotide, and can refer to a variety of distinguishable moieties including zipcodes, a known number of nucleobases, and combinations thereof. In some embodiments, a target-identifying portion, or a target-identifying portion complement, can hybridize to a detector probe, thereby allowing detection of a target polynucleotide sequence in a decoding reaction, such as for example a real-time PCR. In some embodiments, target-identifying portion complements serve as capture moieties for attaching at least one target-identifier portion element complex to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092). Typically, target-identifying portions and their corresponding target-identifying portion complements are selected to minimize: internal, self-hybridization; cross-hybridization with different target-identifying portion species, nucleotide sequences in a reaction composition, including but not limited to gDNA, different species of target-identifying portion complements, or target-specific portions of primary and secondary oligonucleotides, and the like; but should be amenable to facile hybridization between the target-identifying portion and its corresponding target-identifying portion complement. Target-identifying portion sequences and target-identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460–65 (1998)). Descriptions of target-identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides"

therein); U.S. Pat. No. 5,935,793 (referred to as "identifier tags" therein); and PCT Publication No. WO 01/92579 (referred to as "addressable support-specific sequences" therein). In some embodiments non-target specific portion of a primary oligonucleotide can comprise a target-identifying portion, and the detector probe in a real-time PCR can hybridize to the corresponding target-identifying portion during the reaction. In some embodiments, the detector probe can hybridize to both the target-identifying portion as well as sequence corresponding to the target polynucleotide. In some embodiments, at least two target-identifying portion: target-identifying portion complement duplexes have melting temperatures that fall within a $\Delta T_m$ range ($T_{max}-T_{min}$) of no more than 10° C. of each other. In some embodiments, at least two identifying portion: identifying portion complement duplexes have melting temperatures that fall within a $\Delta T_m$ range of 5° C. or less of each other. In some embodiments, at least two identifying portion: identifying portion complement duplexes have melting temperatures that fall within a $\Delta T_m$ range of 2° C. or less of each other. In some embodiments, at least one target-identifying portion complement is annealed to at least one corresponding target-identifying portion and, subsequently, at least part of that target-identifying portion complement is released and detected, as described further for example in Published P.C.T. Application WO04/4634 to Rosenblum et al., Published P.C.T. Application WO01/92579 to Wenz et al., and U.S. Pat. No. 6,759,202.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other places, Sambrook et al. Molecular Cloning, $3^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501–07 (1996); The Nucleic Acid Protocols Handbook, R. Rapley, ed., Humana Press, Totowa, N.J. (2002); Abramson et al., Curr Opin Biotechnol. 1993 February; 4(1):41–7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152–162 (1995), Ehrlich et al., Science 252:1643–50 (1991); Innis et al., PCR Protocols: A Guide to Methods and Applications, Academic Press (1990); Favis et al., Nature Biotechnology 18:561–64 (2000); and Rabenau et al., Infection 28:97–102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188–93 (1991); Bi and Sambrook, Nucl. Acids Res. 25:2924–2951 (1997); Zirvi et al., Nucl. Acid Res. 27:e40i–viii (1999); Dean et al., Proc Natl Acad Sci USA 99:5261–66 (2002); Barany and Gelfand, Gene 109:1–11 (1991); Walker et al., Nucl. Acid Res. 20:1691–96 (1992); Polstra et al., BMC Inf. Dis. 2:18-(2002); Lage et al., Genome Res. 2003 February; 13(2): 294–307, and Landegren et al., Science 241:1077–80 (1988), Demidov, V., Expert Rev Mol Diagn. 2002 November; 2(6):542–8, Cook et al., J Microbiol Methods. 2003 May; 53(2):165–74, Schweitzer et al., Curr Opin Biotechnol. 2001 February; 12(1):21–7, U.S. Pat. No. 5,830,711, U.S. Pat. No. 6,027,889, U.S. Pat. No. 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2, U.S. Pat. No. 5,536,649, and U.S. Provisional Application 60/584,682 to Andersen et al., wherein UNG decontamination and phosphorylation are performed in the same reaction mixture, which further comprises a heat-activatable ligase.). In some embodiments of the present teachings, any of a variety of techniques can be employed prior to amplification in order to facilitate amplification success, as described for example in Radstrom et al., Mol Biotechnol. 2004 February; 26(2):133–46. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein "ligation" comprises any enzymatic or non-enzymatic means wherein an inter-nucleotide linkage is formed between the opposing ends of nucleic acid sequences that are adjacently hybridized to a template. In some embodiments, ligation also comprises at least one gap-filling procedure, wherein the ends of the two probes are not adjacently hybridized initially but the 3'-end of the upstream probe is extended by one or more nucleotide until it is adjacent to the 5'-end of the downstream probe, typically by a polymerase (see, e.g., U.S. Pat. No. 6,004,826). The internucleotide linkage can include, but is not limited to, phosphodiester bond formation. Such bond formation can include, without limitation, those created enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, *Thermus scotoductus* (Tsc) ligase, TS2126 (a thermophilic phage that infects Tsc) RNA ligase, *Archaeoglobus flugidus* (Afu) ligase, *Pyrococcus furiosus* (Pfu) ligase, or the like, including but not limited to reversibly inactivated ligases (see, e.g., U.S. Pat. No. 5,773,258), and enzymatically active mutants and variants thereof. Other internucleotide linkages include, without limitation, covalent bond formation between appropriate reactive groups such as between an α-haloacyl group and a phosphothioate group to form a thiophosphorylacetylamino group, a phosphorothioate a tosylate or iodide group to form a 5'-phosphorothioester, and pyrophosphate linkages. Chemical ligation can, under appropriate conditions, occur spontaneously such as by autoligation. Alternatively, "activating" or reducing agents can be used. Examples of activating and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light, such as used for photoligation. In some embodiments ligation can provide amplification in and of itself, as well as provide for an initial amplification followed by a subsequent amplification. In some embodiments of the present teachings, unconventional nucleotide bases can be introduced into the ligation probes and the resulting products treated by enzymatic (e.g., glycosylases) and/or physical-chemical means in order to render the product incapable of acting as a template for subsequent downstream reactions such as amplification. In some embodiments, uracil can be included as a nucleobase in the ligation reaction mixture, thereby allowing for subsequent reactions to decontaminate carryover of previous uracil-containing products by the use of uracil-N-glycosylase. Various approaches to decontamination using glycosylases and the like can be found for example in Published P.C.T. Application WO9201814A2). Methods for removing unhybridized and/or unligated probes following a ligation reaction are known in the art, and are further discussed supra. Such procedures include nuclease-mediated approaches, dilution, size exclusion approaches, affinity moiety procedures, (see for example U.S. Provisional Application 60/517,470, U.S. Provisional Application 60/477,614, and P.C.T. Application 2003/37227), affinity-moiety procedures involving immobilization of target polynucleotides (see for example Published P.C.T. Application WO 03/006677A2).

As used herein, the term "ligase" and "ligation agent" are used interchangeably and refer to any number of enzymatic or non-enzymatic reagents capable of joining a linker probe to a target polynucleotide. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids. Temperature sensitive ligases, include, but are not limited to, bacteriophage T4 ligase and *E. coli* ligase. Thermostable ligases include, but are not limited to, Afu ligase, Taq ligase, Tfl ligase, Tth ligase, Tth HB8 ligase, *Thermus* species AK16D ligase and Pfu ligase (see for example Published P.C.T. Application WO00/26381, Wu et al., Gene, 76(2):245–254, (1989), Luo et al., Nucleic Acids Research, 24(15): 3071–3078 (1996). The skilled artisan will appreciate that any number of thermostable ligases, including DNA ligases and RNA ligases, can be obtained from thermophilic or hyperthermophilic organisms, for example, certain species of eubacteria and archaea; and that such ligases can be employed in the disclosed methods and kits. Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in, among other places, Xu et al., Nucleic Acid Res., 27:875–81 (1999); Gryaznov and Letsinger, Nucleic Acid Res. 21:1403–08 (1993); Gryaznov et al., Nucleic Acid Res. 22:2366–69 (1994); Kanaya and Yanagawa, Biochemistry 25:7423–30 (1986); Luebke and Dervan, Nucleic Acids Res. 20:3005–09 (1992); Sievers and von Kiedrowski, Nature 369:221–24 (1994); Liu and Taylor, Nucleic Acids Res. 26:3300–04 (1999); Wang and Kool, Nucleic Acids Res. 22:2326–33 (1994); Purmal et al., Nucleic Acids Res. 20:3713–19 (1992); Ashley and Kushlan, Biochemistry 30:2927–33 (1991); Chu and Orgel, Nucleic Acids Res. 16:3671–91 (1988); Sokolova et al., FEBS Letters 232: 153–55 (1988); Naylor and Gilham, Biochemistry 5:2722–28 (1966); and U.S. Pat. No. 5,476,930. Photoligation using light of an appropriate wavelength as a ligation agent is also within the scope of the teachings. In some embodiments, photoligation comprises oligonucleotides comprising nucleotide analogs, including but not limited to, 4-thiothymidine ($s^4T$), 5-vinyluracil and its derivatives, or combinations thereof. In some embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. In some embodiments, photoligation is reversible. Descriptions of photoligation can be found in, among other places, Fujimoto et al., Nucl. Acid Symp. Ser. 42:39–40 (1999); Fujimoto et al., Nucl. Acid Res. Suppl. 1:185–86 (2001); Fujimoto et al., Nucl. Acid Suppl., 2:155–56 (2002); Liu and Taylor, Nucl. Acid Res. 26:3300–04 (1998) and on the world wide web at: sbchem.kyoto-u.ac.jp/saito-lab.

The term "corresponding" as used herein refers to a specific relationship between the elements to which the term refers. Some non-limiting examples of corresponding include: a primary looped linker can correspond with a primary oligonucleotide, and vice versa. The target-specific portion of the primary oligonucleotide can correspond with a target polynucleotide, and vice versa. A mobility probe can correspond with a particular target-identifying portion and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Exemplary Embodiments

Some embodiments of the present teachings comprise methods, compositions, and kits for identifying the alleles present at a SNP locus in a target polynucleotide sequence. For example, in some embodiments, a primary oligonucleotide, which can be considered an allele specific oligonucleotide (ASO) is ligated to a secondary oligonucleotide, which can be considered a locus specific oligonucleotide (LSO), so as to produce a principal ligation product, wherein the ligation event is dependent upon the presence of a particular allele at a SNP locus. A primary looped linker, which can be considered an ASO looped linker, comprising a universal forward priming site, a target-identifying portion, and a blocking moiety, is ligated to the 5' end of the principal ligation product. A secondary looped linker, which can be considered an LSO looped linker, comprising a universal reverse priming site and a blocking moiety, is ligated to the 3' end of the principal ligation product. The ligation events can occur in the same solution, resulting in a nuclease-resistant ligation product comprising the ASO looped linker, the ASO, the LSO, and the LSO looped linker. After ligation, the ligation mixture can be treated with at least one exonuclease to reduce the amount of unligated oligonucleotides and to remove regions of the nuclease-resistant ligation product that are external to the blocking moieties. The nuclease-resistant ligation product can be amplified using primers corresponding with the universal forward and reverse priming portions. In some embodiments, the present teachings can be multiplexed so as to simultaneously detect allelic variants at a plurality of SNP loci, thus allowing a single universal forward and universal reverse primer pair to amplify a plurality of different nuclease-resistant ligation products. Different nuclease-resistant ligation products formed in a multiplexed reaction can be distinguished from one another on the basis of different target-identifying portions present in each ASO.

In some embodiments, the oligonucleotides in a given reaction can be thought of as being organized into distinct sets. One set of oligonucleotides can be considered a variable oligonucleotide set, and another set of oligonucleotides can be considered a fixed oligonuceotide set. For example, the variable oligonucleotide set in a reaction for determining the allelic identity of 48 single nucleotide polymorphism (SNP) loci can comprise 48 ASO pairs, totaling 96 different ASOs, wherein each pair queries a particular genomic locus. As a result of a distinct discriminating nucleotide and a distinct target-identifying portion, one ASO of a given pair encodes one allelic variant of a particular genomic locus, while the other ASO of that pair encodes a different allelic variant of that same genomic locus. The variable oligonucleotide set can further comprise 48 LSO's, wherein each LSO hybridizes to a target polynucleotide sequence at a particular genomic locus, and wherein LSOs hybridizing to adjacent ASOs on the target polynucleotide sequence can be ligated together to form the principal ligation product. In this example, the 144 primary and secondary oligonucleotides together comprise a variable oligonucleotide set. Extending this example, the fixed oligonuceotide set can comprise 96 ASO looped linkers, wherein each linker can be ligated to one ASO of the variable oligonucleotide set, based on the specificity of the hybridization of the single-stranded portion an ASO looped linker with the corresponding non-target specific portion of the ASO. The fixed oligonuceotide set can further comprise 1 LSO looped linker, wherein this LSO looped linker can be ligated to all 48 LSOs of the variable oligonucleotide set as a result of the common non-target specific portion on all 48 LSOs. It will be appreciated from this illustrative example that a potentially infinite number of SNP loci can be queried with an infinite number of variable oligonucleotide sets, while a single fixed set can be applied to any and all of the variable oligonucleotide sets. The following figures can further clarify some of the various embodiments of the present teachings.

FIG. 1 depicts the formation of a concatameric ligation product according to some embodiments of the present teachings. Here, a target polynucleotide (1) comprising a C nucleotide at a SNP position is hybridized to a primary oligonucleotide (62) and a secondary oligonucleotide (63). The primary oligonucleotide (62) contains a 3' G that is complementary with the C at the SNP position of the target polynucleotide (1). A primary looped linker (64) is hybridized to the primary oligonucleotide (62). A secondary looped linker (65) is hybridized to the secondary oligonucleotide (63). A ligation reaction (66) comprising the ligation of the primary looped linker (64) to the primary oligonucleotide (62), the ligation of the primary oligonucleotide (62) to the secondary oligonucleotide (63), and the ligation of the secondary oligonucleotide (63) to the secondary looped linker (65), results in the formation of a concatameric ligation product (67).

Figure 2:
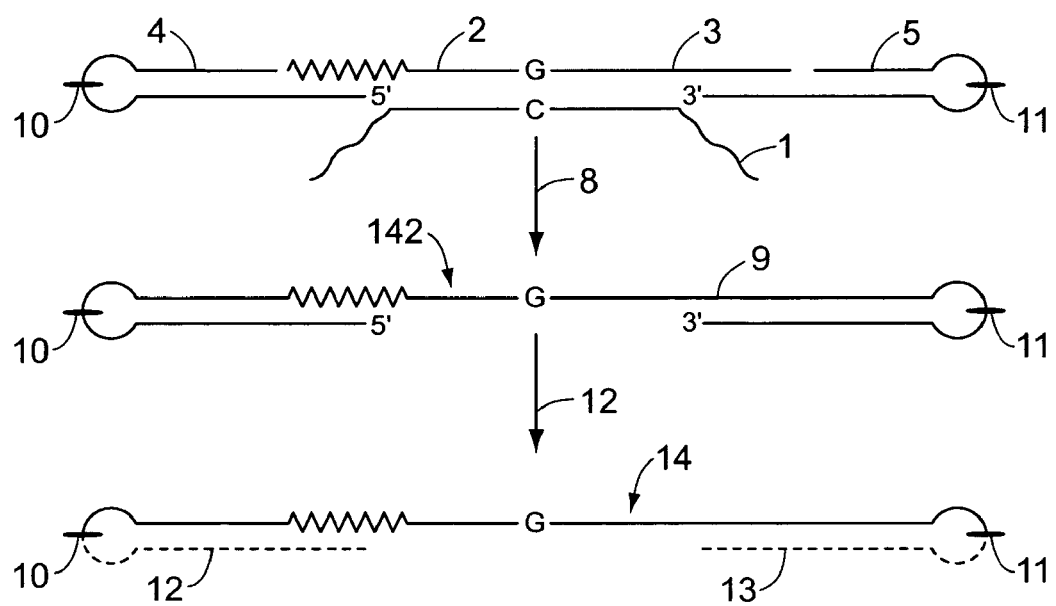
FIG. 2 depicts certain aspects of various compositions according to some embodiments of the present teachings.

FIG. 2 depicts the formation of a nuclease-resistant ligation product according to some embodiments of the present teachings. Here, a target polynucleotide (1) comprising a C nucleotide at a SNP position is hybridized to a primary oligonucleotide (2) and a secondary oligonucleotide (3). A primary looped linker (4) comprising a blocking moiety (10) is hybridized to the primary oligonucleotide (2). A secondary looped linker (5) comprising a blocking moiety (11) is hybridized to the secondary oligonucleotide (3). A ligation reaction (8) is then performed to form a nuclease-resistant ligation product (142) involving ligation of the primary looped linker (4) to the primary oligonucleotide (2), ligation of the primary oligonucleotide (2) to the secondary oligonucleotide (3), and ligation of the secondary oligonucleotide (3) to the secondary looped linker (5). The resistance to nuclease is provided by the blocking moiety on the primary looped linker (10) and/or the blocking moiety on the secondary looped linker (11). Treatment of the nuclease-resistant polynucleotide with nuclease (12) results in degradation of only those regions external to the blocking moieties (dotted line 12, dotted line 13), while those regions internal to the blocking moieties remain intact (14). For example, a 5' acting nuclease such as lambda exonuclease can degrade those regions external to the blocking moiety 10, whereas a 3'-acting nuclease, such as exonuclease 1, can degrade those regions external to the blocking moiety (11). Treatment with both a 5' acting nuclease and a 3' acting nuclease can degrade both the region external to blocking moiety (10) and blocking moiety (11).

Figure 3:
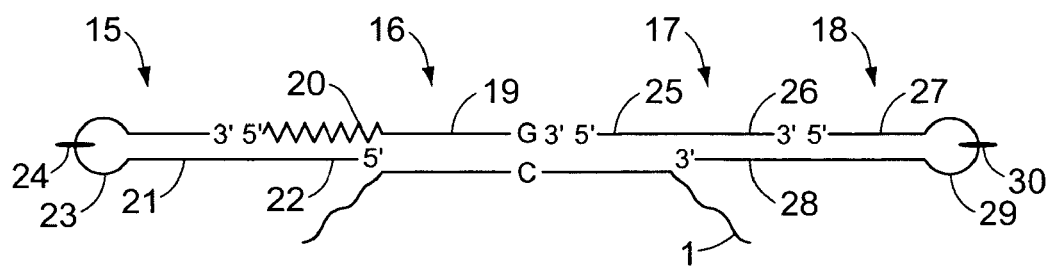
FIG. 3 depicts certain aspects of various compositions according to some embodiments of the present teachings.

FIG. 3 depicts the relationship between a primary looped linker (15), a primary oligonucleotide (16), a secondary oligonucleotide (17), and a secondary looped linker (18), hybridized to a target polynucleotide (1) according to some embodiments of the present teachings. Here, the primary oligonucleotide (16) comprises a target specific portion (19) with a G at its 3' end, and a non-target specific portion (jagged, 20). The primary looped linker (15) comprises a self-complementary portion (21), a single-stranded portion (22), and a loop (23) comprising a blocking moiety (24). The single-stranded portion (22) of the primary looped linker (15) can hybridize with a region of the non-target specific portion (20) of the primary oligonucleotide (16), thereby allowing ligation of the 3' end of the primary looped linker to the 5' end of the primary oligonucleotide. The secondary oligonucleotide (17) comprises a target specific portion (25) and a non-target specific portion (26). The secondary looped linker (18) comprises a self-complementary portion (27), a single-stranded portion (28), and a loop (29) comprising a blocking moiety (30). The single-stranded portion of the secondary looped linker (28) can hybridize with a region of the non-target specific portion of the secondary oligonucleotide (26), thereby allowing ligation of the 3' end of the secondary oligonucleotide to the 5' end of the secondary looped linker.

Figure 4:
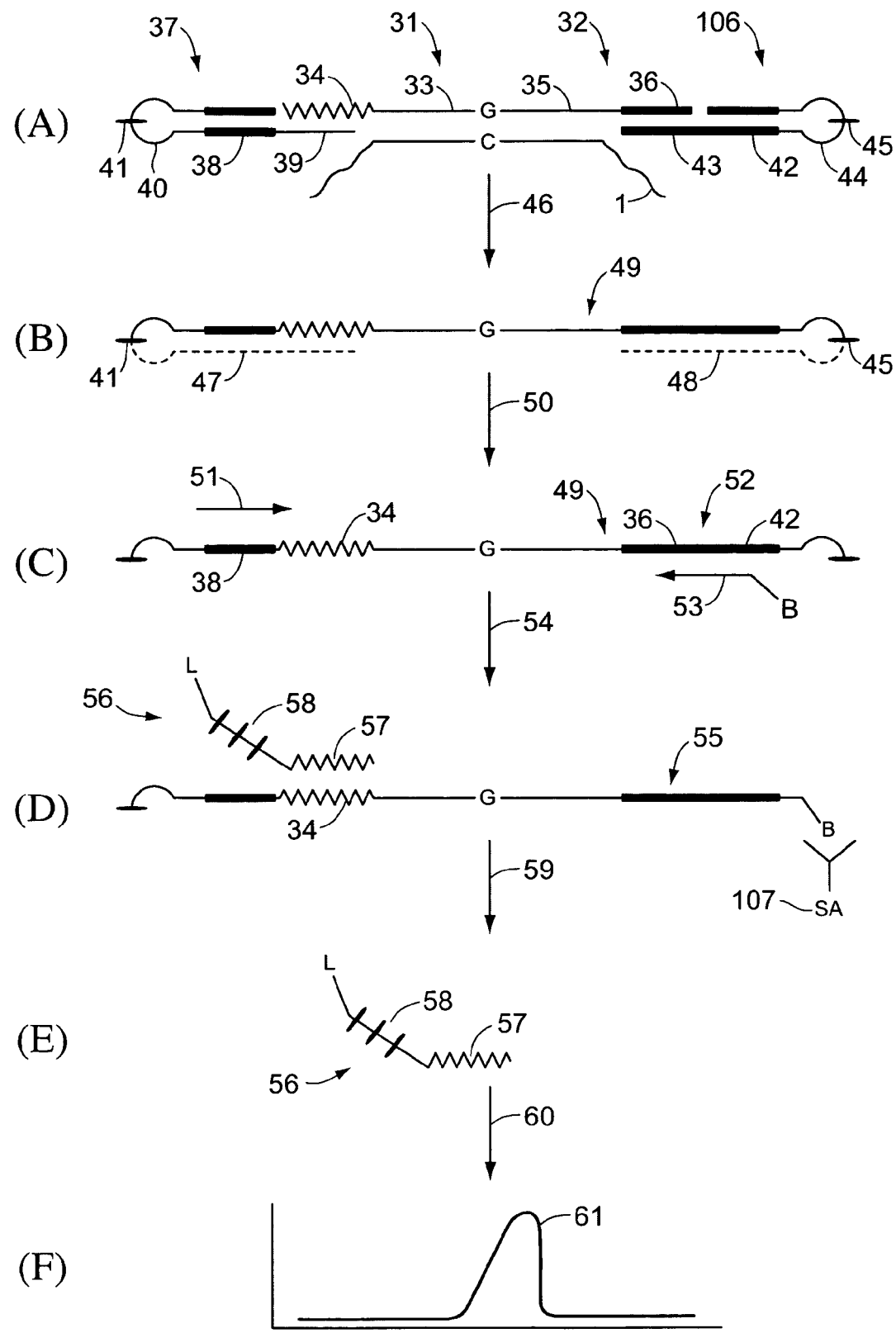
FIG. 4 depicts a method for detecting a target polynucleotide according to some embodiments of the present teachings.

FIG. 4A depicts the formation of a nuclease-resistant ligation product in the context of querying the identity of a single nucleotide polymorphism. Here, a target polynucleotide (1) comprising a C nucleotide at a SNP position is hybridized to a primary oligonucleotide (31) and a secondary oligonucleotide (32). The primary oligonucleotide (31) can be considered an allele-specific oligonucleotide (ASO) and comprises a target specific portion (33) with a G nucleotide at its 3' end, and a non-target specific portion (34). The non-target specific portion (34) can function as a target-identifying portion. The primary looped linker (37) comprises a self-complementary portion (38), a single-stranded portion (39), and a loop (40) comprising a blocking moiety (41). The single-stranded portion (39) can hybridize with a region of the non-target specific portion of the primary oligonucleotide (34), thereby allowing ligation of the 3' end of the primary looped linker to the 5' end of the primary oligonucleotide. The secondary oligonucleotide (32) can be considered a locus specific oligonucleotide (LSO), and comprises a target specific portion (35) and a non-target specific portion (36). When the primary oligonucleotide (31) and secondary oligonucleotide (32) are hybridized to adjacent regions on the target polynucleotide (1), they can be ligated together. The secondary looped linker (106) comprises a self-complementary portion (42), a single-stranded portion (43), and a loop (44) comprising a blocking moiety (45). The single-stranded portion (43) can hybridize with a region of the non-target specific portion of the secondary oligonuceotide (36), thereby allowing ligation of the 3' end of the secondary oligonucleotide to the 5' end of the secondary looped linker. Following ligation of the primary looped linker (37) to the primary oligonucleotide (31), ligation of the primary oligonucleotide (31) to the secondary oligonucleotide (32), and ligation of the secondary oligonucleotide (32) to the secondary looped linker (106), a nuclease-resistant ligation product can be formed (49).

FIG. 4B depicts the effects of nuclease treatment of the nuclease-resistant ligation according to some embodiments of the present teachings. Here, nuclease treatment (46) of the nuclease-resistant polynucleotide results in degradation of only those regions external to the blocking moieties (dotted line 47, dotted line 48), while those regions internal to the blocking moieties remain in tact (49). For example, a 5'-acting nuclease, such as lambda exonuclease can degrade those regions external (47) to the blocking moiety (41), whereas a 3'-acting nuclease, such as exonuclease 1, can degrade those regions external (48) to the blocking moiety (45). (46) represents treatment with both a 5' acting nuclease and a 3' acting nuclease wherein both the region external to blocking moiety (41) and blocking moiety (45) are degraded.

FIG. 4C depicts a PCR amplification (50) of the nuclease-resistant ligation product (49) according to some embodiments of the present teachings. Here, the functions of sequence information contained within the primary looped linker, the primary oligonucleotide, the secondary oligonucleotide, and the secondary looped linker become apparent as the reaction proceeds with a PCR amplification (50). For example, the resulting self-complementary region of the primary looped linker (38) now single-stranded, can correspond to a forward PCR primer (51). The non-target specific portion of the primary oligonucleotide (34) can serve as a target-identifying portion. Ligation of the 3' end of the non-target specific portion of the secondary oligonucleotide (36) to the 5' end of the self-complementary portion of the secondary looped linker (42) resulted in the formation of a complete sequence corresponding to a reverse PCR primer site (52), thus allowing for PCR amplification with a reverse primer (53), shown here containing the affinity moiety biotin (B).

FIG. 4D depicts hybridization of a mobility probe to an immobilized amplification product according to some embodiments of the present teachings. Here, the results of amplification, immobilization, and hybridization of a mobility probe are shown (54). For example, the biotin-containing amplification product (55) is shown immobilized on a solid support comprising streptavidin (107, SA). A mobility probe (56) is shown, wherein the target-identifying portion (34) of the amplification product is hybridized to a complementary target-identifying portion (57) in the mobility probe. The mobility probe (56) further comprise a mobility modifier (58) and a label (L).

FIG. 4E depicts elution of the mobility probe, according to some embodiments of the present teachings. Here, the eluted (59) mobility probe (56) can be detected with a mobility dependent analysis technique such as capillary electrophoresis. The association between the target-identifying portion (34) and a particular target polynucleotide that was encoded in the ligation reaction (FIG. 4A), is thus decoded here in FIG. 4E using capillary electrophoresis based on the distinct mobility modifier (58) and label (L) that is characteristic of the corresponding mobility probe (56).

FIG. 4F depicts the result of a mobility dependent analysis technique (60) according to some embodiments of the present teachings. Here, a capillary electrophoresis trace (61) is shown, wherein the mobility probe is detected at a particular location, as determined by its mobility modifier. The mobility probe is further detected with a particular color, as determined by its label.

Figure 5:
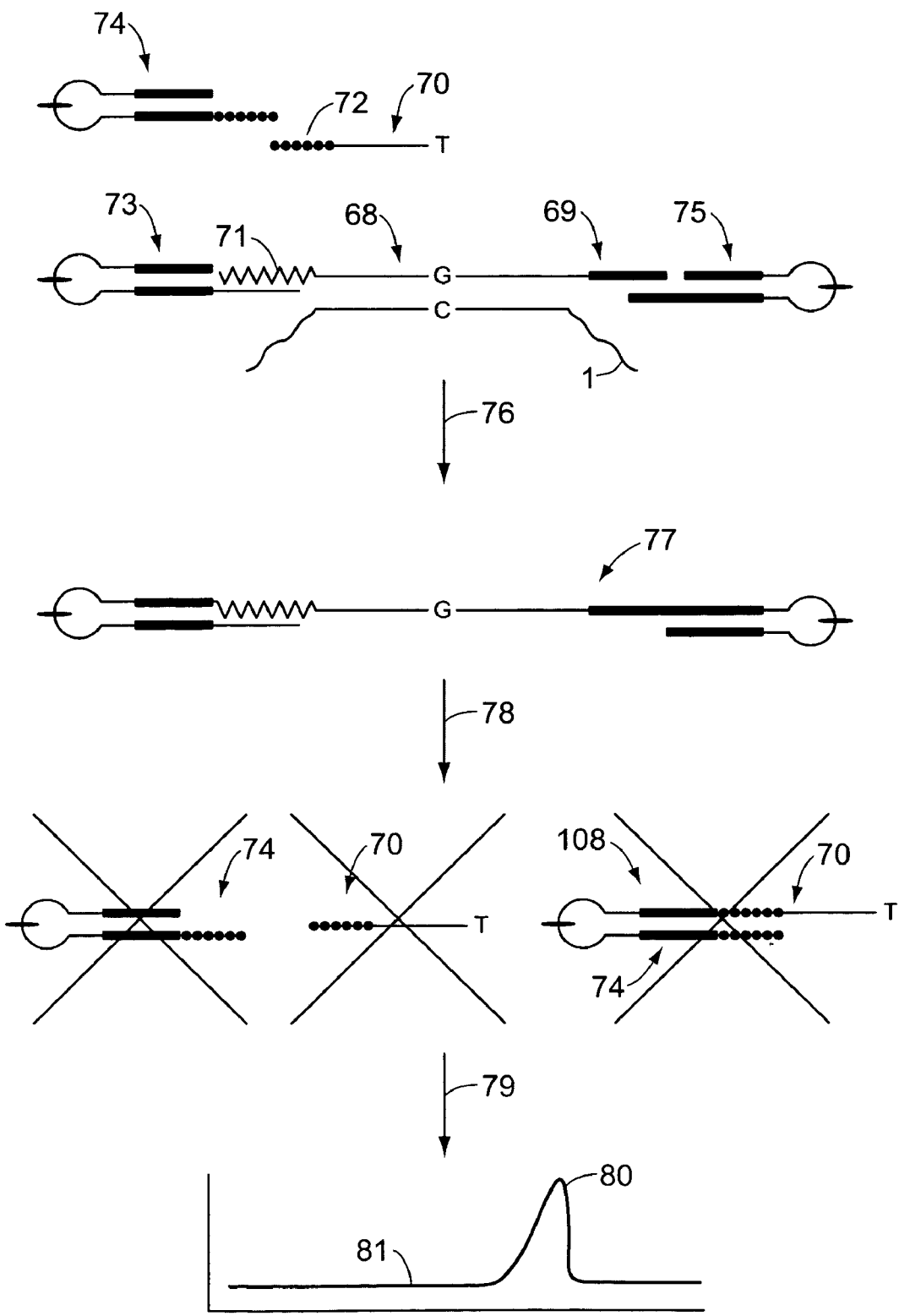
FIG. 5 depicts a method for detecting a target polynucleotide according to some embodiments of the present teachings.

FIG. 5 depicts the detection of a particular allele at a SNP position according to some embodiments of the present teachings. Here, a target polynucleotide (1) comprising a C nucleotide at a SNP position is hybridized to a first primary oligonucleotide (68) and a secondary oligonucleotide (69). The first primary oligonucleotide (68), comprising a G nucleotide at the 3'-end of the target-specific portion, can be considered an allele-specific oligonucleotide (ASO1). The second primary oligonucleotide (70), comprising a T nucleotide at the 3'-end of the target specific portion, can be considered an allele-specific oligonucleotide (ASO2). As shown, the ASO2 does not hybridize to the target (1) since the allele of the target comprises a C at the SNP position and the T of ASO2 is not complementary. The first primary oligonucleotide (68) further comprises a non-target specific portion (71), and the second primary oligonucleotide (69) further comprises a non-target specific portion (72). The non-target specific portion of the first primary oligonucleotide (71) can function as a target-identifying portion enconding the C allele, and the non-target specific portion of the second primary oligonucleotide (72) can function as a target-identifying portion encoding the A allele. Also shown is a first primary looped linker (73) that can hybridize with the first primary oligonucleotide (68), and a second primary looped linker (74) that can hybridize with the second primary oligonucleotide (70). Also shown is a secondary oligonucleotide (69) that can be considered a locus specific oligonucleotide (LSO), and a secondary looped linker (75). A ligation reaction (76) comprising ligation of the first primary oligonucleotide (68) to the first primary looped linker (73), ligation of the first primary oligonucleotide (68) to the secondary oligonucleotide (69), and ligation of the secondary oligonucleotide (69) to the secondary looped linker (75) results in the formation of a nuclease-resistant ligation product (77). Treatment with 5'-acting and 3'-acting nucleases (78) results in degradation of the non-ligated second primary looped linker (74, left crossed through circle), degradation of the non-ligated second primary oligonucleotide (70, middle crossed through circle), and degradation of ligation product (108) comprising second primary looped linker (74) and second primary oligonucleotide (70, right crossed through circle). Other non-incorporated species can also be degraded (not shown), including regions of the nuclease resistant ligation product that are external to the blocking moieties. The nuclease-resistant ligation product, or surrogate thereof such as an eluted mobility probe, can be detected by a mobility dependent analysis technique such as capillary electrophoresis (79), wherein a peak representing the C allele is present (80), and a peak representing an A allele is absent (81).

Figure 6:
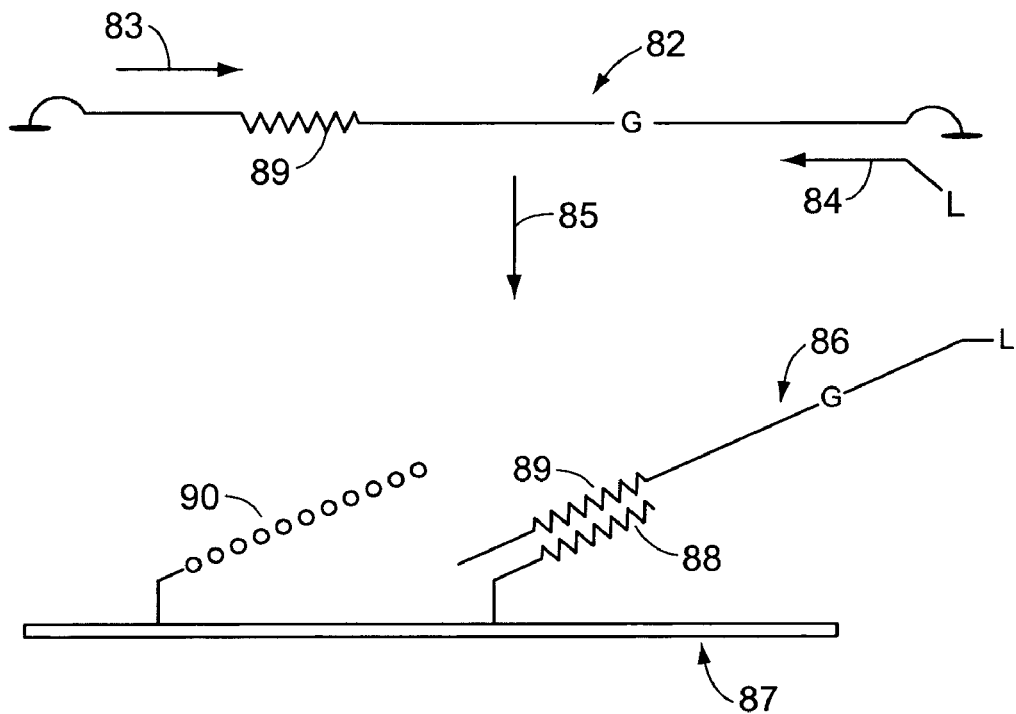
FIG. 6 depicts a method for detecting a target polynucleotide according to some embodiments of the present teachings.

FIG. 6 depicts the detection of a particular allele at a SNP position with an array, according to some embodiments of the present teachings. Here, a nuclease-resistant ligation product (82) can be PCR amplified with a forward primer (83) and a reverse primer (84) containing a label (L). Following amplification and any purification procedures (85), the labeled amplification product (86) can be detected on a solid support such as an array (87), wherein for example an immobilized oligonucleotide (88) complementary to a target-identifying portion (89) allows for capture and detection of the amplification product (86). An immobilized oligonucleotide that is not complementary to any target-identifying portion in amplification product (90) will not be detected, indicating the absence of a corresponding target polynucleotide.

Figure 7:
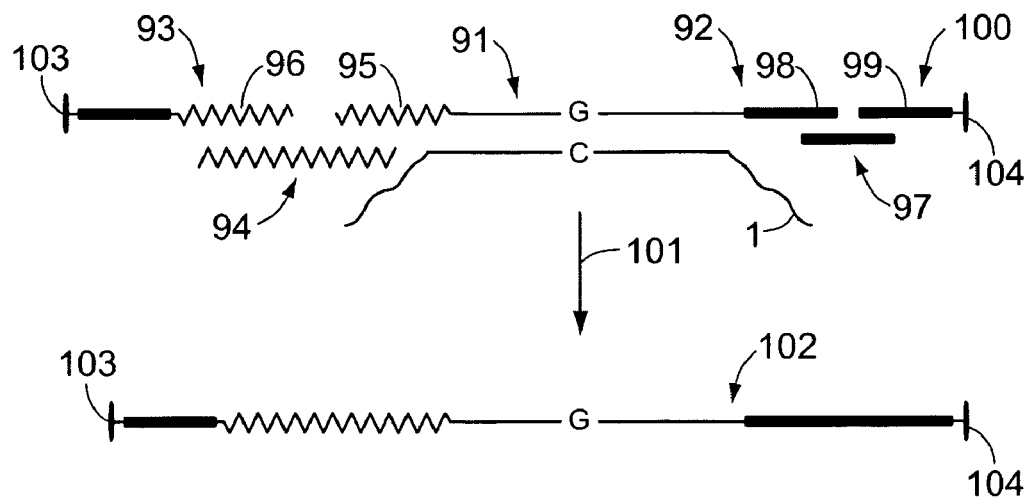
FIG. 7 depicts certain aspects of various compositions according to some embodiments of the present teachings.

FIG. 7 depicts the formation of a nuclease-resistant ligation product according to some embodiments of the present teachings. Here, linear oligonucleotides are employed. Shown is a target polynucleotide (1) containing a C nucleotide at a SNP position. A primary oligonucleotide (91) comprising a 3' G nucleotide, and a secondary oligonucleotide (92), are hybridized on the target polynucleotide (1). A primary splint linker oligonucleotide (94) can hybridize with a non-target specific portion (jagged, 95) of the primary oligonucleotide (91) and the primary splint linker oligonucleotide (94) can hybridize with the 3' end region (jagged, 96) of the primary distal linker oligonucleotide (93), thereby allowing ligation of the 3' end of the primary distal linker oligonucleotide (93) with the 5' end of the primary oligonucleotide (91). A secondary splint linker oligonucleotide (97) can hybridize with a non-target specific portion of the secondary oligonucleotide (98) and the secondary splint linker oligonucleotide (97) can hybridize with the 5' end region of a secondary distal linker oligonucleotide (99), thereby allowing ligation of the 3' end of the secondary oligonucleotide with the 5' end of the secondary distal linker oligonucleotide. A ligation reaction (101) comprising ligation of the primary distal linker oligonucleotide (93) to the primary oligonucleotide (91), ligation of the primary oligonucleotide (91) to the secondary oligonucleotide (92), and ligation of the secondary oligonucleotide (92) to the secondary distal linker oligonucleotide (100) results in the formation of a nuclease-resistant ligation product (102). Treatment with nucleases results in degradation of molecules not incorporated into the nuclease-resistant ligation product, whereas a blocking moiety on the primary distal linker oligonucleotide (103) and/or a blocking moiety on a secondary distal linker oligonucleotide (104) can prevent degradation of the nuclease-resistant ligation product. It will be appreciated that in a manner analogous to the looped linker compositions and methods discussed supra, a target-identifying portion and primer portions can be included in the linear molecules (jagged lines and rectangles, respectively in FIG. 7), to allow for the amplification and detection of the nuclease-resistant ligation product in the myriad ways discussed in the present teachings (for example FIG. 8), and readily known by one of ordinary skill in the art.

Figure 8:
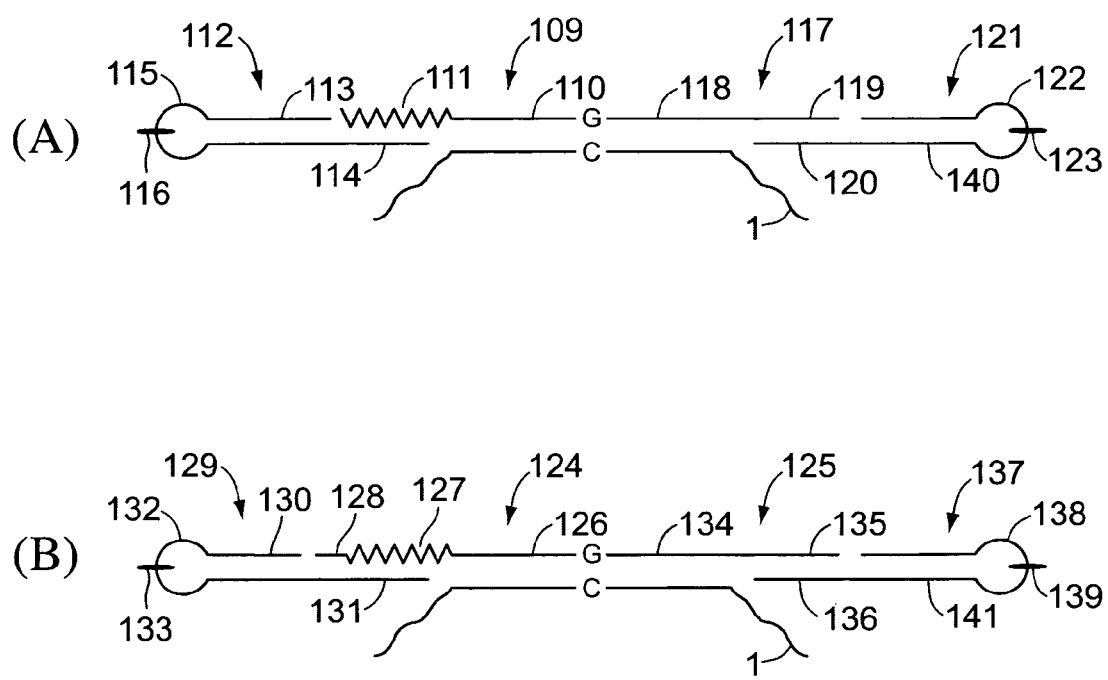
FIG. 8 depicts certain aspects of various compositions according to some embodiments of the present teachings.
Figure 9:
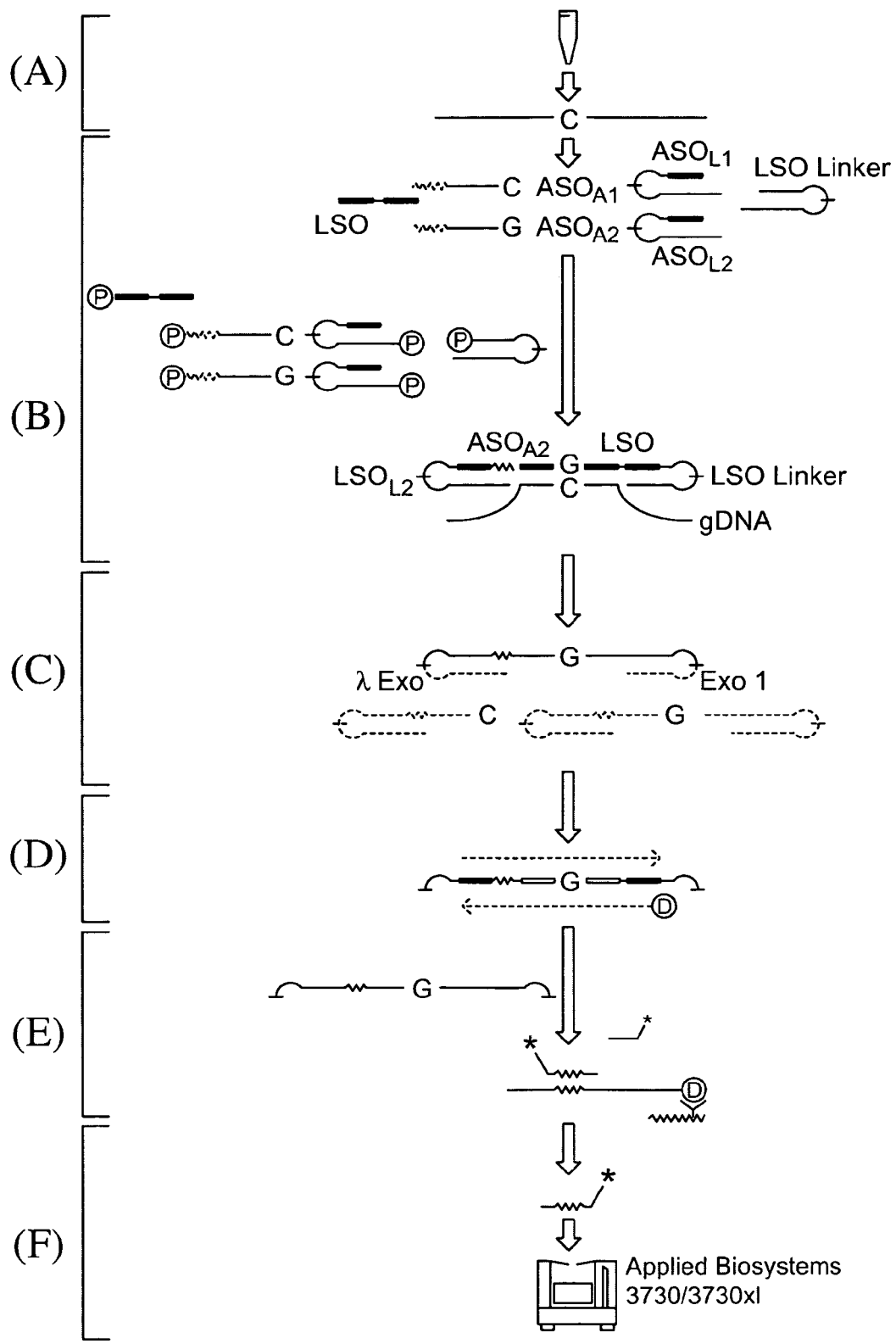
FIG. 9 depicts an overview of some embodiments of the present teachings.

FIG. 8 depicts various functional regions of the oligonucleotides according to some embodiments of the present teachings. For example, the functions provided by the target-identifying portion and primer portion of a primary oligonucleotide and a primary looped linker can be fulfilled in a variety of ways. Depicted in FIG. 8A, the primary oligonucleotide (109) and the secondary oligonucleotide (117) are hybridized on a target polynucleotide (1). The primary oligonucleotide (109) contains a 3' G that is complementary with the C at the SNP position of the target polynucleotide (1). The primary oligonucleotide (109) can comprise a target specific portion (110), and a target-identifying portion (111, jagged). The primary looped linker (112) comprises a self-complementary portion (113), as well as a single stranded portion (114) complementary to the target-identifying portion of the primary oligonucleotide (111), thereby allowing hybridization and ligation of the primary oligonucleotide (109) to the primary looped linker (112). The primary looped linker further comprises a loop (115) and a blocking moiety (116). The secondary oligonucleotide (117) comprises a target specific portion (118) and a non-target specific portion (119). The target specific portion of the primary oligonucleotide (110) can ligate with the target specific portion of the secondary oligonucleotide (118). The non-target specific portion of the secondary oligonucleotide can hybridize with the single-stranded portion of the secondary looped linker (120), thereby allowing ligation of the secondary looped linker (121) with the secondary oligonucleotide (117). The secondary looped linker further comprises a loop (122), a blocking moiety (123), and a self-complementary portion (140).

Depicted in FIG. 8B, the primary oligonucleotide (124) and the secondary oligonucleotide (125) are hybridized on a target polynucleotide (1). The primary oligonucleotide (124) contains a 3' G that is complementary with the C at the SNP position of the target polynucleotide (1). The primary oligonucleotide (124) can comprise a target specific portion (126), a target-identifying portion (127, jagged), and a partial forward primer portion (128). The primary looped linker (129) comprises double stranded forward primer portion (130), and a single stranded portion (131) that is complementary to both the partial forward primer portion of the primary oligonucleotide (128) and a region of the target identifying portion of the primary oligonucleotide (127), thereby allowing hybridization and ligation of the primary oligonucleotide (124) to the primary looped linker (129). The primary looped linker further comprises a loop (132) and a blocking moiety (133). The secondary oligonucleotide (125) comprises a target specific portion (134) and a non-target specific portion (135). The target specific portion of the primary oligonucleotide (126) can ligate with the target specific portion of the secondary oligonucleotide (134). The non-target specific portion of the secondary oligonucleotide (135) can hybridize with the single-stranded portion of the secondary looped linker (136), thereby allowing ligation of the secondary looped linker (137) with the secondary oligonucleotide (125). The secondary looped linker further comprises a loop (138), a blocking moiety (139), and a self-complementary portion (141).

Extending on the teachings of FIG. 8, the present teachings further contemplate other embodiments in which other sliding placement shifts in the functions of the oligonucleotides are performed in order to achieve the generation of a concatameric ligation product consistent with the context of the present teachings. In some embodiments, a constant tag sequence can be inserted between the target identifying portion and a partial forward primer portion of a primary oligonucleotide, and the primary looped linker hybridized to a plurality of different primary oligonucleotides can be the same for each of the different primary oligonucleotides used to query a plurality of allelic variants. Additional modifications are possible, and such procedures are within routine experimentation of one of ordinary skill in the art armed with the present teachings.

Some illustrative and non-limiting oligonucleotide lengths can be considered in light of FIG. 8A. For example, the primary looped linker (112) comprises a single-stranded portion (114) of about 20 nucleotides that is complementary to a region of the target-identifying portion of the primary oligonucleotide (111, jagged). (It will be appreciated that here, as elsewhere in the present teachings, when discussing that the primary looped linker (112) can comprise a single-stranded portion (114) of about 20 nucleotides that is complementary to a "region" of the target-identifying portion of the primary oligonucleotide (111, jagged), that the term "region" can refer to some, or all, of the target identifying portion). The primary looped linker (112) further comprises a self-complementary portion (113) of about 16 nucleotides. The 16 nucleotides of the self-complementary portion (113) together with 5 nucleotides of the loop (115) internal to a C18 blocking moiety can function as a forward primer portion. The primary oligonucleotide (109) can comprise a target-specific portion (110) of about 20 nucleotides and a non-target specific portion (111, jagged) of about 24–26 nucleotides, wherein the non-target specific portion (111, jagged) can function as a target-identifying portion. A secondary oligonucleotide (117) can comprise a target specific portion (118) of about 12–20 nucleotides, and a non-target specific portion (119) of about 16 nucleotides, wherein the 16 nucleotides of the non-target specific portion (119) along with about 5 nucleotides of the self-complementary portion of the secondary looped linker (140) can function as a reverse primer portion. The remainder of the self-complementary portion assists in molecular stability. The loop of the secondary looped linker (122) comprises a blocking moiety (123) comprising 5'UUGAAAUU, wherein the U's comprise 2'-O-methyl uracil. Further, the melting temperature Tm of a primary looped linker/primary oligonucleotide can be about 60–65 C, and the Tm of a secondary looped linker/secondary oligonucleotide can be about 60–65 C.

Some illustrative and non-limiting oligonucleotide lengths can also be considered in light of FIG. 8B. For example, the primary looped linker (129) comprises a single-stranded portion (131) of about 20 nucleotides that is complementary to both a region of the target-identifying portion of the primary oligonucleotide (127, jagged) and a region of the primary probe comprising a partial forward primer portion (128) of about 4–6 nucleotides. The primary looped linker (129) further comprises a self-complementary portion (130) of about 16 nucleotides. The 16 nucleotides of the self-complementary portion (113) together with about 5 nucleotides of the loop (115) internal to a C18 blocking moiety, and 4–6 nucleotides of the partial forward primer portion (128) of the primary probe (128), can function as a forward primer portion. The primary oligonucleotide (124) can comprise a target-specific portion (127) of about 20 nucleotides, a non-target specific portion (127, jagged) of about 24–26 nucleotides wherein the non-target specific portion (127, jagged) can function as a target-identifying portion, and a partial forward primer portion of about 4–6 nucleotides (128). A secondary oligonucleotide (125) can comprise a target specific portion (134) of about 12–20 nucleotides, and a non-target specific portion (135) of about 16 nucleotides, wherein the 16 nucleotides of the non-target specific portion (135) along with about 5 nucleotides of the self-complementary portion (141) can function as a reverse primer portion. The remainder of the self-complementary portion can assist in molecular stability. The loop of the secondary looped linker (138) comprises a blocking moiety (139) comprising 5'UUGAAAUU, wherein the U's comprise 2'-O-methyl uracil. Further, the melting temperature Tm of a primary looped linker/primary oligonucleotide can be about 60–65 C, and the Tm of a secondary looped linker/secondary oligonucleotide can be about 60–65 C.

It will be appreciated by one of ordinary skill in the art that routine experimentation, along with the present teachings in hand, can produce a variety of nucleotide lengths for the functional portions of the oligonucleotides of the present teachings.

Nuclease-Mediated Clean-Up of Unligated Oligonucleotides:

Nuclease-mediated digestion of unincorporated reaction components can be performed according to the present teachings in order to remove unincorporated reaction components, as well as degrade regions of the nuclease-resistant ligation product external to the blocking moieties. The digestion of unincorporated reaction components can be used to minimize spurious interactions between these molecules in an amplification reaction such PCR, thereby reducing unwanted background products such as primer dimers. Additionally, the nuclease-mediated digestion of portions of the nuclease-resistant ligation product external to the blocking moieties provides for the generation of single stranded regions on which PCR primers can hybridize, thereby further increasing the specificity of the amplification reaction. Exemplary blocking moieties comprise C3, C9, C12, and C18, available commercially from Glen Research, tetra methoxyl uracil, as well as moieties described for example in U.S. Pat. No. 5,514,543, and Woo et al., U.S. application Ser. No. 09/836,704. Exemplary nucleases comprise exonuclease 1 and lambda exonuclease, which act on the 3' and 5' ends, respectfully, of single stranded oligonucleotides. Other enzymes as appropriate for practicing the present teachings are readily available to one of ordinary skill in the art, and are commercially available from such sources as New England Biolabs, Roche, and Stratagene.

For example, primary looped linkers that are incorporated into nuclease resistant ligation products can be sensitive to 5'-acting nuclease digestion proceeding from their 5' ends to the blocking moiety, thereby allowing for the generation of a single stranded area on which a PCR primer can eventually hybridize. Moreover, primary group looped linkers that are not incorporated into concatameric ligation products are sensitive to both 5'-acting nuclease digestion proceeding from their 5' ends to the blocking moiety, as well as sensitive to 3'-acting nuclease digestion proceeding from their free 3' ends. Further, primary group looped linkers that are ligated to ASO's, but which are not incorporated into a full concatameric ligation product, are also sensitive to both 3'-acting degradation via the ASO, as well as directly via 5'-acting nucleases.

In some embodiments, secondary looped linkers that are incorporated into nuclease-resistant ligation products can be sensitive to 3'-acting nuclease digestion proceeding from their 3' ends to the blocking moiety, thereby allowing for the generation of a single stranded area on which a PCR primer can eventually hybridize. Moreover, secondary group looped linkers that are not incorporated into concatameric ligation products are sensitive to both 5' acting nuclease digestion proceeding from their 5' ends to the blocking moiety, as well as sensitive to 3'-acting nuclease digestion proceeding from their free 3' ends to the blocking moiety. Further, secondary looped linkers that are ligated to LSO's, but which are not incorporated into a concatameric ligation product are also sensitive to 3'-acting nucleases directly, as well 5'-acting nucleases via degradation through the LSO.

In some embodiments the primary looped linker can comprise C18 as a blocking moiety. In some embodiments, the secondary looped linker can comprises 2'-O-methyluracil as a blocking moiety.

In some embodiments, the primary distal linker can comprises a blocking moiety at or near its 3' end. In some embodiments, the secondary distal linker can comprise a blocking moiety at or near its 5' end. Those distal oligonucleotides that are incorporated into concatameric ligation products can be resistant to nuclease digestion, whereas distal oligonucleotides that are not incorporated into a concatameric ligation product can be sensitive to nuclease digestion, and can be removed from the reaction mixture.

In some embodiments the primary distal linker can comprise C18 as a blocking moiety. In some embodiments, the secondary distal linker can comprises 2'-O-methyl-uracil as a blocking moiety.

It will further be appreciated that the present teachings contemplate embodiments in which looped linkers and single stranded linkers are used concurrently. For example, looped linkers can be used on the ASO side, whereas single stranded linkers can be used on the LSO side. The converse is also contemplated, in which looped linkers can be used on the LSO side, whereas single stranded linkers can be used on the ASO side. Additionally, both looped linkers and single stranded linkers can be used together on the same side, in a multiplexed reaction querying a plurality of target polynucleotides.

Detection of Concatameric Ligation Products:

In some embodiments, nuclease treatment of nuclease-resistant ligation products can be followed by a PCR amplification, wherein the reverse primer contains an affinity moiety such as biotin. The biotinylated strand of the resulting double stranded amplified concatameric ligation product can be immobilized, and a mobility probe hybridized thereon. After washing, the mobility probes can be analyzed on a capillary electrophoresis instrument and the identity and quantity of the target polynucleotide sequence determined. Exemplary capillary electrophoresis instruments useful with the present teachings include the Applied Biosystems 3100, 3700, and 3730xl DNA sequencers. Additional discussion of the detection of concatameric ligation products in the context of multiplexed SNP analysis can be found in the commercially available SNPlex User Manual, available from Applied Biosystems.

It will be appreciated that the present teachings contemplate any of a variety of ways of determining the presence and/or quantity and/or identity of a target polynucleotide. In some embodiments employing a donor moiety and signal moiety, one may use certain energy-transfer fluorescent dyes, for example in real-time PCR approaches. Certain non-limiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as detector probes include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™ (all available from Applied Biosystems, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal, as for example in U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide. As used herein, determining the presence of a target can comprise identifying it, as well as optionally quantifying it. In some embodiments, the amplification products can be scored as positive or negative as soon as a given number of cycles is complete. In some embodiments, the results may be transmitted electronically directly to a database and tabulated. Thus, in some embodiments, large numbers of samples can be processed and analyzed with less time and labor when such an instrument is used. In some embodiments, different detector probes may distinguish between different target polynucleotides. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different target-identifying portions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' may form even if the appropriate target nucleic acid sequence is not in the sample, but such occurs to a measurably lesser extent than when the appropriate target nucleic acid sequence is in the sample. After amplification, one can determine which specific target polynucleotide sequences are present in the sample based on the wavelength of signal detected and their intensity. Thus, if an appropriate detectable signal value of only wavelength $WL_A$ is detected, one would know that the sample includes target polynucleotide A, but not target polynucleotide B. If an appropriate detectable signal value of both wavelengths $WL_A$ and $WL_B$ are detected, one would know that the sample includes both target polynucleotide A and target polynucleotide B. In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target polynucleotide determined via a mobility dependent analysis technique of the eluted mobility probes, as described for example in Published P.C.T. Application WO04/46344 to Rosenblum et al., and WO01/92579 to Wenz et al., and U.S. Pat. No. 6,759,202. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251–62, 1999; De Bellis et al., Minerva Biotec 14:247–52, 2002; and Stears et al., Nat. Med. 9:140–45, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings. Further, it will be appreciated that detection of a target polynucleotide includes detecting surrogates of the target polynucleotide. Some examples of a surrogate include but are not limited to, a reporter group that was cleaved from a TaqMan® probe during a nuclease assay can be detected and thus indicates that target polynucleotide is present, a labeled amplified ligation product can be detected on an array, and, a mobility probe can be hybridized to a target-identifying portion, eluted, and detected by a mobility dependent analysis technique (see for example U.S. Pat. No. 6,759,202).

In some embodiments of the present teachings, the target-identifying portion incorporated into a concatameric ligation product can be queried with a chimeric D-DNA/L-DNA probes. Those chimeric probes with a D-DNA portion that hybridize with target-identifying portions of the nuclease-resistant ligation product can be eluted, and the L-DNA portion of the chimeric probe detected on an array comprising complementary L-DNA molecules. Array detection can occur via any suitable means. For example, chimeric D-DNA/L-DNA probes comprising a florophore can be detected on the array with florescence. Various approaches for using L-DNA for detection of target polynucleotides are discussed for example in Published U.S. Application US2003/0198980A1. The present teachings further contemplate embodiments in which D-DNA/L-DNA chimeric probes further comprise mobility modifiers, such that detection of eluted probes can be achieved with either a mobility dependent analysis technique or an array.

Oligonucleotide Composition:

In some embodiments of the present teachings, the oligonucleotides of the primary and secondary groups are comprised of DNA. It will be appreciated by one of skill in the art that various advantages can be conferred to the thermodynamic and kinetic properties of the oligonucleotides through the use of nucleic acid analogs, including embodiments in which the pentose sugar and/or the nucleotide base and/or one or more of the phosphate esters of a nucleoside may be replaced with its respective analog. In some embodiments of the present teachings, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions. Some embodiments of the present teachings further comprise analog monomers that can be polymerized into polynucleotide analogs in which the DNA/RNA phosphate ester and/or sugar phosphate ester backbone is replaced with a different type of linkage. Exemplary polynucleotide analogs include, but are not limited to, peptide nucleic acids, in which the sugar phosphate backbone of the polynucleotide is replaced by a peptide backbone. In some embodiments of the present teachings, oligonucleotides may be comprised of LNA (Mouritzen et al., 2003), and/or comprised of PNA (Chen et al., U.S. Pat. No. 6,469,151) and/or comprised of L-DNA. In some embodiments of the present teachings, oligonucleotides may be comprised of other nucleic acid analogs and bases, for example intercalating nucleic acids (INAs, as described in Christensen and Pedersen, 2002), and AEGIS bases (Eragen, U.S. Pat. No. 5,432,272). In some embodiments of the present teachings, chimeric oligonucleotides are employed comprising both DNA as well as at least one DNA analog.

In some embodiments, the 3' discriminating position of the ASO's can comprise an LNA moiety, thereby decreasing misligation in sample reactions. In some embodiments, the 3' discriminating position of the ASO's can comprise an LNA moiety thereby decreasing misligation in negative control reactions wherein target polynucleotide sequence is absent.

It will be appreciated that the introduction of varying amounts of nucleic acid analogs and varying olignucleotide length can be exploited to alter the melting temperature of the oligonucleotides in such ways as necessary to optimize the hybridization reaction conditions and/or minimize non-specific hybridization, and that such optimization falls within the reasonable scope of laboratory endeavors of one having ordinary skill in the art of molecular biology.

In some embodiments of the present teachings, the target-identifying portion is comprised of a defined number of nucleotides or nucleotide analogs, thereby conferring a distinct size to a given concatameric ligation product. The identity of the target polynucleotide sequence is determined by the characteristic mobility of the concatameric ligation product as exhibited in a mobility dependent analysis technique.

In some embodiments, the discriminating nucleotide in the target polynucleotide sequence may comprise additional nearby nucleotides that differ as well. For example, an unwanted SNP may be near a SNP of interest, thereby making it difficult to design an ASO that can query the desired SNP without the complicating effects of nearby SNPs. Such complicating effects include the potential disruption of hybridization of a primary and/or secondary oligonucleotide with a target polynucleotide. In some embodiments, the present teachings contemplate the use of universal DNA base analogues (see Loakes, N.A.R. 2001, vol 29:2437–2447, Seela N.A R. 2000, vol 28:3224–3232, Published U.S. Patent Application 2003/0198980, and Published P.C.T. Application WO03/040395A2, and U.S. Provisional application Ser. No. 10/877,511) to mask these nearby polymorphisms. Such approaches can facilitate uniformity in annealing conditions for ASOs targeting a specific target polynucleotide sequence that contains a variant close to the targeted SNP. For example, U.S. Provisional application Ser. No. 10/877,511 describes universal nucleotides that can hybridize with comparable efficiency with the different nucleotides A,T,G, and C, and also be incorporated into an extension reaction product (e.g. a PCR product). Such an approach can result in an amplified ligation product comprising the different nucleotides at the universal nucleotide position. In some embodiments, the present teachings contemplate the use of 2'-deoxy-1'-(3-allenyl-7-azaindole-1-nyl) ribose as a universal nucleotide in a primary oligonucleotide, a secondary oligonucleotide, or a primary oligonucleotide and a secondary oligonucleotide, wherein the 2'-deoxy-1'-(3-allenyl-7-azaindole-1-nyl) ribose corresponds with a unwanted SNP that resides near a SNP of interest. Illustrative teachings for the synthesis and use of this universal nucleotide can be found in U.S. Provisional application Ser. No. 10/877,511 and Published P.C.T. Application WO03/040395A2.

Preparation, Amplification and Detection of Concatameric Ligation Products:

In some embodiments, the resulting concatameric ligation product can be amplified by taking advantage of the resulting incorporated universal forward and reverse primer portions. The amplified concatameric ligation product can be identified and quantified based on the sequence information of the target-identifying portion.

It will further be appreciated that the oligonucleotides of the variable oligonucleotide set and the fixed oligonuceotide set may be synthesized in situ to include a 5' phosphate group exploited by ligase biochemistry. The 5' phosphate group can also be introduced through a kinase reaction, for example through the use of T4 polynucleotide kinase. In some embodiments, the kinase reaction can further comprise an enhancer, for example PEG 8000, or any suitable water excluding molecule. It will be appreciated that the present teachings may be applied in the context of a variety of hybridization and ligation strategies for multiplexed analysis of target polynucleotide sequences, including for example various combinations of LDR (ligase detection reaction) and PCR, see U.S. Pat. Nos. 5,494,810 and 6,027,889, (see U.S. Pat. No. 5,185,243, European Patent Applications EP 32038 and EP 439182, published PCT Patent Application WO 90/01069 and WO 96/15271, U.S. Provisional applications 60/427,818, 60/445,636, 60/445,494, WO 97/31256, U.S. Pat. Nos. 6,027,889, 6,268,148, 5,494,810, 5,830,711, 6,054,564, WO 97/31256, U.S. Ser. Nos. 01/17329, 10/620, 332, 10/620,333, U.S. Pat. Nos. 4,988,617 and 5,830,711, 4,683,202, 4,683,195 and 4,965,188) various gap ligation strategies wherein gaps located between oligonucleotides may be filled in by polymerase-mediated extension. Such gaps may be present between the distal linker/looped linker and ASO's of the primary group, and/or the ASO of the primary group and the LSO of the secondary group, the LSO of the secondary group and the distal linker/looped linker of the secondary group, or combinations thereof.

In some embodiments of the present teachings, a secondary ligation reaction may be performed using the concatenated ligation product as a template in order to determine the identity of the target polynucleotide sequence (see U.S. application 60/477,614).

In some embodiments of the present teachings, phosphorylysis may be employed to remove non-ligatable overhanging nucleotides at the 3' end of the ASO, thereby generating a complex suitable for ligation (Liu and Sommer, 2002).

In some embodiments of the present teachings, complementary oligonucleotides to the ASO, ASO looped linker, LSO, and LSO looped linker can be employed, resulting in the exponential amplification of the target polynucleotide sequence in an LCR-type procedure (see U.S. Pat. No. 5,494,810), or, with overlapping oligonucleotide probes in a FEN-LCR-type procedure (see U.S. Pat. No. 6,511,810).

In some embodiments of the present teachings, the ligation reaction and PCR amplification reaction can occur in the same closed tube (see U.S. Pat. No. 5,912,148) wherein the melting temperature of the PCR primers differs from the melting temperature of the ligation probes, thereby allowing selection of OLA and/or LDR cycling parameters with the ligation oligonucleotides occur is prior to the onset of a different annealing temperature for PCR cycling with the amplification primers.

In some embodiments of the present teachings, ligation-competent complexes are ligated together using a variety of procedures, including enzymatic and chemical methods. Numerous ligase enzymes are known in the art and can be obtained from a variety of biological and commercial sources. Exemplary ligases include, but are not limited to, *E. coli* ligase, T4 ligase, *T. aquaticus* ligase, AK16D (U.S. application 9925437), *T. Thermophilus* ligase, Pfu ligase, etc. (see, for example, U.S. Pat. No. 5,830,711 (Barany et al.) and EP Patent 320308 B1 (Backman and Wang). In some embodiments of the present teachings, a thermostable ligase is used and the need to replenish ligase activity during temperature cycling attenuated. In some embodiments of the present teachings, the thermostable ligase retains at least 80% of initial 5' nuclease activity after thirty cycles of 65° C. for 1 min. (annealing/extension) and 95° C. for 15 seconds (strand denaturation).

In some embodiments of the present teachings, unligated oligonucleotides can be removed from the ligation mixture prior to an amplification reaction. Removal of unligated oligonucleotides prior to amplification can reduce primer-dimer amplification reaction side products as well as result in a more accurate amplification reaction with fewer background products. As described supra, blocking moieties can be incorporated into oligonucleotides of the ligation reaction, thereby imparting varying sensitivity and/or resistance to nuclease degradation. In some embodiments, unligated oligonucleotides can be removed by employing treatment of target polynucleotide sequences in such fashion as to allow for their immobilization. For example, genomic DNA can be biotinylated, and hybridization of oligonucleotides can then be performed. Unhybridized oligonucleotides can then be removed from the reaction, and ligation of remaining hybrized oligonucleotides can then be performed (see Forster et al., 1985, and more generally Hermanson Bioconjugate Techniques, 1996, as well as commercial products from Pierce).

In some embodiments of the present teachings, the target polynucleotide sequences can be amplified prior to hybridization of the primary and secondary sets via a pre-amplification strategy, as described inter alia in U.S. application 60/431,156 and U.S. Pat. No. 6,605,451. Such pre-amplification strategies can allow for an increased ability to query large numbers of target polynucleotides with limited amounts of starting sample material. A variety of amplification strategies are contemplated, including but not limited to PCR-based strategies, multiple strand displacement based strategies, and T7 RNA polymerase-based strategies.

In some embodiments of the present teachings, detection, identification, and quantification of the one or more target polynucleotide sequences can be achieved following primer-mediated amplification of the concatameric ligation product. In some embodiments, the target-identifying portion of the amplified concatameric ligation product can serve as the template for a complementary mobility probe. The mobility probe can further comprise a mobility modifying moiety and a label (see for example U.S. Pat. No. 5,777,096), whereby the identify of the one or more target polynucleotides can be determined and quantified by the unique mobility of the mobility probe as assessed by a mobility dependent analysis technique, for example capillary electrophoresis on an ABI 3730xl (also see U.S. applications 60/427,818, 60/445,636, 60/445,494).

In some embodiments of the present teachings, detection, identification, and quantification of the one or more target polynucleotide sequences can be achieved following primer-mediated amplification of the concatameric ligation product, wherein one of the primers further comprises a detectable label. In some embodiments, the target-identifying portion of the amplified concatameric ligation product can form a complementary double stranded species with an array-immobilized substrate, and the target polynucleotide sequence determined from the resulting location and label (see Published U.S. Application U.S. 97/01535, Published U.S. application Ser. No. 09/584,905, and Published U.S. application Ser. No. 10/313,505, and U.S. Pat. No. 6,506,594).

In some embodiments, the amplification reaction further comprises uracil instead of, or in addition to, thymine. Amplicons resulting from PCR performed in the presence of uracil are susceptible to degradation with the nuclease uracil N-glycosylase (see U.S. Pat. No. 5,418,149). In some embodiments of the present teachings, the ligation reaction can be performed in the presence of uracil N-glycosylase in order to degrade contaminant amplicons from earlier performed PCR experiements.

In some embodiments, the present teachings further comprise a single universal primer that is the same for both the forward primer and the reverse primer.

In some embodiments of the present teachings, amplification of the concatameric ligation product is performed with a primer pair in which one of the primers has an incorporated biotin moiety. By binding the resulting PCR product to a streptavidin solid support, the PCR product can be immobilized, and unbiotiylated unincorporated primers as well as other unincorporated reaction components can be washed away. The immobilized amplification product can be melted, such that the non-biotinylated strand is released and washed away. The remaining bound biotinylated strand can then serve as a single-stranded substrate for hybridization of the mobility probe. It will be appreciated that any number of affinity moiety-binding pairs can be used in the spirit of the present teachings, with biotin-streptavidin being but one illustrative example (see for example Hermanson, 1996). Further, it will be appreciated that a variety of solid supports can be employed in a manner consistent with the present teachings, including bead-based procedures and plate-based procedures.

In some embodiments of the present teachings, the nucleic acid sample comprising the target polynucleotide sequences can be treated with photo biotin. Following immobilization of the biotinylated target polynucleotides, and hybridization of the primary and secondary groups, unybridized oligonucleotides can be washed away from the bound hybridized target polynucleotide sequences, thereby allowing for a pre-ligation removal of unhybridized oligonucleotides (Hermanson Bioconjugate Techniques, 1996).

In some embodiments of the present teachings, the concatameric ligation product can be hybridized with a mobility probe further comprising a mobility modifer, a label, and nucleotides encoding a target-identifying portion. In some embodiments, LNA and/or PNA can be included in the mobility probe. By increasing the Tm per unit length of an oligonucleotide, the presence of varying amounts of LNA and/or PNA can result in added stringency per unit length. By including LNA and/or PNA, the overall length, and potentially cost, of a mobility probe can be reduced.

In some embodiments, the present teachings employ mobility dependent analysis techniques (or MDAT) to analyze and determine the identity and quantity of the target polynucleotide sequence. MDAT refers to an analytical technique based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like.

In some embodiments, the present teachings employ oligonucleotide array techniques to analyze and determine the identity and quantity of the target polynucleotide sequence. Exemplary arrays can be found from Applied Biosystems' 1700 system, Agilent, Affymetrix, Rosetta, Illumina and the like, as well as a variety of homebrew arrays constructed in a variety of academic and government centers. See for example U.S.97/01535, U.S. application Ser. No. 09/584,905, U.S. application Ser. No. 10/313,505, and U.S. Pat. No. 6,506,594, and WO 02101358, WO 03048732, WO 0157268, and WO 0157269. In some embodiments, immobilized oligonucleotides in a non-array type format can used in a manner similar to arrays, for example oligonucleotides immobilized on labeled beads, see for example published U.S. application Ser. No. 10/302,688.

Application Areas:

It will be appreciated that the application area in which the present teachings can apply is virtually unlimited. In some embodiments of the present teachings, the one or more target polynucleotides can comprise genomic loci with potential single nucleotide polymorphisms (SNPs), and the teachings applied to determining the identity and quantity of allelic variants at a plurality of SNP loci. In some embodiments, the identified SNP loci can function to identity a human in a forensics setting. In some embodiments, the identified SNP loci can function to identify a pathogenic microorganism in a clinical diagnostic setting. In some embodiments, the one or more target polynucleotides can comprise expressed genes (mRNA), which can be converted into cDNA for more convenient analysis, and the teachings applied to ascertaining the identity and quantity of expressed genes. In some embodiments, the one or more target polynucleotides comprise splice variants of mRNA, which can be converted into cDNA, and the teachings applied to ascertaining the identity and quantity of expressed splice variants. In some embodiments, the one or more target polynucleotides comprise methylated DNA, or methylated DNA that has been treated to distinguish methylated cytosine from unmethylated cytosine, and the teachings applied to ascertaining the identity and quantity of methylated cytosine. In some embodiments, the one or more target polynucleotides comprise micro RNA and/or small interfering RNA, and the teachings applied to ascertaining the identity and quantity of micro and/or small interfering RNA. In some embodiments of the present teachings, the one or more target polynucleotides can comprise expressed genes (mRNA), and the teachings applied to ascertaining the identity and quantity of expressed genes (Landegren, N.A.R. 29(2):578–81).

The present teachings can be applied in a basic research setting, a clinical diagnostic setting for evaluated disease susceptibility genes, an plant agricultural setting for determination of pedigree or genetic modified organism (GMO) status, a animal livestock agricultural setting for determination of pedigree or GMO status, forensic setting to determine human identity, microorganism pathology setting to determine type and pathogenicity of a microorganism, and more generally in any setting in which the determination, identification, and quantification of one or more target polynucleotide sequences is desired.

Kits:

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

The present teachings comprise novel compositions for achieving the generation of the concatameric ligation product that can be presented as kits. In some embodiments, the present teachings contemplate kits comprising a variable oligonucleotide set, kits comprising a fixed oligonucleotide set, a ligase, a kinase, a uracil-N-glycosylase, 3'-acting nucleases, 5'-acting nucleases, 3' and 5' acting nucleases, buffers, amplification primers, polymerases, mobility probes, or combinations thereof. The present teachings also contemplate kits comprising other reagents and compositions as necessary to perform the methods of the present teachings.

Some embodiments of the present teachings provide a means for ligating, a means for nuclease-mediated digesting, a means for amplifying, a means for detecting, or combinations thereof.

Compositions:

In some embodiments, the present teachings provide a concatameric ligation product comprising a primary looped linker ligated to a primary oligonucleotide, the primary oligonucleotide ligated to a secondary oligonucleotide, and the secondary oligonucleotide ligated to a secondary looped linker.

In some embodiments, the present teachings provide a looped linker composition comprising a self-complementary portion, a loop, and a single-stranded portion, wherein the single-stranded portion corresponds to a target-identifying portion in a primary oligonucleotide, wherein the self-complementary portion comprises a primer portion. In some embodiments, the primer portion is a universal primer portion.

In some embodiments, the present teachings provide a looped linker composition comprising a self-complementary portion, a loop, and a single-stranded portion, wherein the single-stranded portion corresponds to a non-target specific portion in a secondary oligonucleotide, wherein the self-complementary portion comprises a primer portion. In some embodiments, the primer portion is a universal primer portion.

In some embodiments, the present teachings provide a mixture comprising a first looped linker composition and a second looped linker composition; wherein the first looped linker composition comprises a self-complementary portion, a loop, and a single-stranded portion, wherein the single-stranded portion of the first looped linker composition corresponds to a region of a target-identifying portion in a first primary oligonucleotide and wherein the self-complementary portion comprises a primer portion; wherein the second looped linker composition comprises a self-complementary portion, a loop, and a single-stranded portion, wherein the single-stranded portion of the second looped linker composition corresponds to a region of a target-identifying portion in a second primary oligonucleotide and wherein the self-complementary portion comprises a primer portion; wherein the primer portion in the first looped linker composition is the same as the primer portion in the second looped linker composition, and, wherein the single-stranded portion of the first looped linker is different from the single-stranded portion of the second looped linker.

In some embodiments, the present teachings provide a nuclease-resistant ligation product comprising a primary looped linker ligated to a primary oligonucleotide, the primary oligonucleotide ligated to a secondary oligonucleotide, and the secondary oligonucleotide ligated to a secondary looped linker, wherein the primary looped linker comprises a blocking moiety, the secondary looped linker comprises a blocking moiety, or the primary looped linker and the secondary looped linker comprise a blocking moiety. In some embodiments, the nuclease-resistant polynucleotide is treated with a nuclease, and a portion external to the blocking moiety is degraded by the nuclease.

In some embodiments, the present teachings provide a looped linker composition comprising a self-complementary portion, a loop, and a single-stranded portion, wherein the single-stranded portion corresponds to a region of a target-identifying portion in a primary oligonucleotide, wherein the self-complementary portion comprises a primer portion, and wherein the loop comprises a blocking moiety. In some embodiments, the primer portion is a universal primer portion.

In some embodiments, the present teachings provide a looped linker composition comprising a self-complementary portion, a loop, and a single-stranded portion, wherein the single-stranded portion corresponds to a region of a non-target-identifying portion in a secondary oligonucleotide, wherein the self-complementary portion comprises a primer portion, and wherein the loop comprises a blocking moiety. In some embodiments, the primer portion is a universal primer portion.

In some embodiments, the present teachings provide a mixture comprising a first looped linker composition and a second looped linker composition, wherein the first looped linker composition comprises a self-complementary portion, a loop, and a single-stranded portion, wherein the single-stranded portion of the first looped linker composition corresponds to a region of a target-identifying portion in a first primary oligonucleotide, wherein the self-complementary portion comprises a primer portion, and wherein the loop comprises a blocking moiety, wherein the second looped linker composition comprises a self-complementary portion, a loop, and a single-stranded portion, wherein the single-stranded portion of the second looped linker composition corresponds to a region of a target-identifying portion in a second primary oligonucleotide, wherein the self-complementary portion comprises a primer portion, and wherein the loop comprises a blocking moiety, wherein the primer portion in the first looped linker composition is the same as the primer portion in the second looped linker composition, and, wherein the single-stranded portion of the first looped linker is different from the single-stranded portion of the second looped linker.

In some embodiments, the present teachings provide a nuclease-resistant ligation product comprising a primary distal linker ligated to a primary oligonucleotide, the primary oligonucleotide ligated to a secondary oligonucleotide, and the secondary oligonucleotide ligated to a secondary distal linker, wherein the primary distal linker and/or the secondary distal linker comprise a blocking moiety.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLE 1

Prepare and Fragment gDNA:

Purify gDNA according to standard procedures (see Applied Biosystems NucPrep, for example) and dilute purified DNA to a concentration of 50–200 ng/ul using 1×TE, pH 8.0. Dispense 12.5 to 150 ul of prepared gDNA into a chilled reaction plate, then cover the plate. Program the thermal cycler as follows: 4 C for 1 minute, 99 C for 10 minutes, 4 C indefinite. When the thermal cycler has reached 4 C, insert the chilled reaction plate and resume the program. After the program is complete, verify the fragment size by running an aliquot on a 0.8% agarose gel. Determine the concentration of the fragmented gDNA, then dilute the fragmented gDNA to a final concentration of 18.5 ng/ul. Dispense 2 ul of diluted DNA into each well of a 384-well optical reaction plate. Air-dry for three days in the dark. After drying, keep the plate covered until use.

Phosphorylate the ASOs, LSOs, and Looped Linkers:

Scale the volumes listed below to the desired number of phosphorylation reactions. Extra volume should be prepared to account for losses which may occur during pipetting.

| Component | Volume per Reaction (uL) |
|---|---|
| variable oligonucleotide set | .10 |
| fixed set | .050 |
| nuclease-free water | .1125 |
| Kinase buffer (10×) | .050 |
| Enhancer | .100 |
| DATP (10 mM) | .0625 |
| Total | .5000 |

Program the termal cycler as follows: 37 C for 1 hour, 4 C indefinite. When the thermal cycler reaches 37 C, load the plates. Dilute the activated oligonucleotide sets with 0.5 ul 0.1×TE Buffer. Store at −20 C until use.

Perform Oligonucleotide Ligation Reaction:

Prepare an OLA master mix by scaling the volumes listed below to the desired number of OLA reactions.

| Component | Vol per Rxn with UNG | Vol per Rxn w/out UNG |
|---|---|---|
| Nuclease-free water | 3.422 | 3.475 |
| 10× Ligation Buffer | .500 | .500 |
| Ligase | .025 | .025 |
| UNG | .053 | — |
| Total | 4.000 | 4.000 |

Prepare the OLA reaction at 4 C by adding the following components to each well of a 384 well containing air-dried gDNA: 4.0 uL OLA master mix (with or without UNG) and 1.0 uL activated OLA probe pool. Use a heat-seal cover to cover the plate, then if using UNG, incubate the plate at 4 C for 10 minutes. After incubation, place the plate on a thermal cycler that has reached 90 C. If not using UNG, keep the plate at 4 C until the thermal cycler has reached 90 C. Run the thermal cyler with 3 minutes 90 C, 30 cycles of 90 C-15 sec, 60 C-30 sec, and 51 C, 2% ramp, 30 sec, followed by 10 min of 99 C, followed by 4 C indefinite.

Prepare Ligation Product by Exonuclease Digestion:

Prepare 2× Exonuclease master mix by scaling the volumes listed below to the desired number of OLA reactions. Prepare extra volume to account for pipetting losses.

| Component | Volume per Reaction (uL) |
| --- | --- |
| Nuclease-free water | 4.2 |
| Buffer (10X) | .5 |
| Lamba exonuclease | .2 |
| Exonuclease I | .1 |
| Total | 5.0 |

Pipette 5.0 uL of 2× exonuclease master mix into each well of the OLA reaction, vortex the plates, and spin briefly. Cover the plate. When the thermal cycler reaches the first hold temperature of 37 C, transfer the reaction plates to the thermal cycler, and start the program. 37 C for 90 minutes, 80 for 10 minutes, and 4 C indefinite. Dilute the exonuclease reactions by adding 15 ul nuclease-free water to each well. Proceed to PCR amplification immediately. Otherwise, store the reactions at −20 C for processing within 24 hours or at −80 C for processing after 24 hours.

PCR Amplify the Ligated and Exonuclease Digested Products:

Prepare a PCR master mix by scaling the volumes listed below to the desired number of PCR reactions. Prepare extra volume to account for pipetting losses.

| Component | Volume per Reaction (uL) |
| --- | --- |
| Nuclease-free water | 2.42 |
| Amplification master mix (2X) | 5.00 |
| Amplification primers (20X) | .500 |
| Total Volume | 7.92 |

Dispense the following into each well of a 384-well plate: 7.92 uL PCR master mix+2.08 uL diluted OLA reaction product from earlier. Cover the plate. When the thermal cycler reaches its first hold temperature of 95 C, transfer the reaction plates to the thermal cycler and start the program. 95 C-10 minutes, followed by 30 cycles of 95 C-15 sec, 70 C-60 sec, followed by a 4 C hold indefinitely. Proceed to bind the amplicons to streptavidin-coated plates immediately. Otherwise, store the reactions at −20 C for processing within 24 hours or at −80 C for processing after 24 hours.

Bind Biotinylated Amplicons to Streptavidin-Coated Plates:

Wash the wells of the hybridization plates three times with 100 ul hybridization wash buffer diluted 1:10. Add 17.5 ul of hybridization binding buffer containing 0.1 nM positive control to the hybridization plate. Transfer 1.5 ul of each well containing the PCR reaction product into the hybridization plate, mix, and cover the plates. Incubate at room temperature for at least 30 minutes on a rotary shaker. Briefly spin the plates and remove the supernatant. Wash three times with 100 uL hybridization wash buffer diluted 1:10. Add 50 uL of 0.1 N NaOH, and incubate for 5 minutes at room temperature on a rotary shaker. Briefly spin the plates and remove the supernatant. Wash five times with 100 uL hybridization wash buffer diluted 1:10.

Hybridize the Mobility Probes to the Target-Identifying Portions:

Equilibrate the oven to 37 C. Prepare a hybridization master mix by scaling the volumes below to the desired number of samples. Prepare extra volume to account for pipetting losses.

| Component | Volume per reaction (uL) |
| --- | --- |
| Mobility probe mix | .05 |
| Denaturant | 11.25 |
| Mobility probe dilution buffer | 13.70 |
| Total | 25.00 |

Add 25 uL of the hybridization master mix to each well of the hybridization plate, and cover. Incubate the plates for 60 minutes at 37 C on a rotary shaker.

Prepare Size Standards, Elute the Mobility Probes, and Dispense the Allelic Ladder:

Prepare a sample loading mix by scaling the volumes listed below to the desired number of samples. The sample loading mix should be freshly prepared each day.

| Component | Volume per reaction (uL) |
| --- | --- |
| Size standard | .59 |
| Sample loading reagent | 16.91 |
| Total | 17.5 |

Briefly spin the plates and remove the supernatant. Wash four times with 100 ul hybridization buffer diluted 1:10. Spin the plates upside down at 1000 rpm for 60 seconds on a stack of paper towels. Add 17.5 uL of sample loading mix into each well and mix. Cover the plates and incubate at 37 C for 30 minutes. Transfer 7.5 uL from each well into a new 384-well optical reaction plate. Pipette 2 uL of the allelic ladder, diluted 1:250.

Perform Electrophoresis and Analyze Data:

Start the 3730/xl data collection software (Applied Biosystems). Create a plate record. Make sure to select GeneMapperGeneric in the application field and Septa in the Plate Sealing field of the New Plate dialog box. Load the plates into the 3730/xl instrument, ensuring that the plate assembly fits flat in the stacker. Program the electrophoresis conditions, as follows.

| Parameter | Value |
| --- | --- |
| Injection voltage and time | 1.0 kV/5 sec |
| Run time | 330 |
| Run voltage | 15 kV. |
| Oven temperature | 60 C. |
| Polymer | Pop-7 |

Run the plates. Analyze your data using GeneMapper™ software v3.5 (Applied Biosystems. Refer to the GeneMapper Software v3.5 online help system for more information about using the software.

EXAMPLE 2

Kinase Reaction:

In some embodiments of the present teachings, a kinase reaction can be performed in which a phosphate group is added to the 5' end of oligonucleotides. Oligonucleotides at 100 nM each can be mixed into a 10 ul volume, to which is added 2 ul 10× Kinase Buffer, 2.5 ul 10 mM dATP, and 1 ul (10 units/ul) T4 Kinase (NEB), and 4.5 ul $dH_2O$, for a total reaction volume of 20 ul. The reaction mixture is mixed and spun briefly and is incubated at 36 C for 1 hour. The kinase is inactivated by incubating at 80 C for 10 minutes. The phosphorylated oligonucleotides are diluted 3-fold by adding 2× volume of dH2O.

Oligonucleotide Ligation Reaction:

In some embodiments of the present teachings, an OLA reaction mix is prepared on ice, comprising 2.7 ul of genomic DNA (18.5 ng/ul), 2 ul of the diluted kinased oligonucleotides, 1 ul 10×OLA Buffer, 1 ul (40 units/ul) ligase, and 3.3 ul $ddH_2O$ in a total reaction volume of 10 ul. The reaction is mixed, and spun briefly, and cycling is performed according to 90 C for 3 minutes, followed by 60 cycles of 90 C/10 second-57 C/60 seconds, followed by 99 C for 10 minutes, ending with a 4 C hold indefinitely.

Nuclease Removal of Unligated Oligonucleotides:

In some embodiments of the present teachings, a 2× nuclease mixture is prepared comprising 0.2 ul lamba exonuclease (5 units/ul), 0.1 ul exonuclease 1 (20 units/ul), 0.35 ul lamba exonuclease buffer (NEB), and 2.85 ul $dH_2O$. Then, 3.5 ul of this 2× nuclease mixture is added to 3.5 ul of OLA products, mixed and spun briefly, and is incubated for 37 C for one hour, followed by 80 C for 10 minutes, ending with a 4 C hold indefinitely.

PCR Amplification:

In some embodiments of the present teachings, the nuclease-digested OLA is diluted 3× by adding 14 ul $dH_2O$. A 10 ul PCR reaction mix is then made comprising 3 ul of the diluted OLA, 5 ul of standard PCR master mix comprising 0.5 ul UA11/UL19 (10 uM each primers) and 1.5 ul $H_2O$. After mixing and spinning briefly, the mixture is heated to 95 C for 10 minutes, followed by 33 cycles of 95 C/10 seconds-68 C/60 seconds, followed by a 4 C hold indefinitely.

Post-PCR Purification:

In some embodiments, a post-amplification purification is performed by adding 10 uL of SAV-Mag beads ($10^7$ beads/uL, 0.7 um diameter, Seradyn) to the 10 uL amplification reaction mixture and incubated at ambient temperature for 10–30 minutes. Next, 10 uL of 0.1M NaOH is added and the resulting mixture is incubated at ambient temperature for 10–20 minutes. After the incubation, a magnet is placed near the bottom of the mixture for 0.5–2 minutes, and the supernatant is removed by micropipette.

Mobility Probe Hybridization and Detection:

For detection of the different amplified ligation products, mobility probes can be prepared for hybridization to the target-identifying portion or target-identifying portion complement of the amplified strands, such that each mobility probe can be used to identify a particular target polynucleotide for which the corresponding oligonucleotide set was successfully ligated and amplified. For example, each mobility probe can comprise a target-identifying portion or target-identifying portion complement comprising a polynucleotide sequence (e.g., 22–26 nt) that is specific for the corresponding target-identifying portion or target-identifying portion complement in one of the amplified strands. Each mobility probe additionally comprises a mobility defining moiety that imparts an identifying mobility (e.g., for electrophoretic detection) or total mass (e.g. for detection by mass spectrometry) to the mobility probe. For example, the mobility probe for each different target sequence may comprise a polyethylene glycol (PEO) polymer segment having a different length (EO)n, where n ranges from 1 to 10. For fluorescence detection, the mobility probes may additionally include fluorescent dyes, such as FAM and VIC dyes, for detection of the different, alternative SNPs at each target locus. These may be attached by standard linking chemistries to the "5' end" of the mobility defining moiety (the end of the mobility defining moiety that is opposite to end that is linked to the target-identifying portion or target-identifying portion complement).

The mobility probes may be hybridized to amplified strands as follow. To the bead-immobilized amplification products is added 10 uL of a mixture of mobility probes (final concentration 100 pM to 1 nM each, or 100 pM to 10 nM each, or 100 pM to 100 nM each) in 4×SSC buffer containing 0.1% SDS), and the resulting mixture is incubated at 50° C. 60° C. for 30 minutes. After the incubation, 100–200 uL 1×PBS buffer containing 0.1% Tween-20 is added. After the mixture is vortexed, a magnet is placed near the bottom of the mixture tube for 2 minutes, and the supernatant is removed by micropipette, and this process of adding PBS buffer, vortexing, and removing supernatant is repeated twice more. A final wash is performed with 0.1× PBS containing 0.1% Tween-20, followed by vortexing and removal of supernatant. To the beads are added 10 uL of DI-formamide solution (Applied Biosystems) and 0.25 uL of size standards (LIZ 120™, Applied Biosystems). The resulting mixture is heated to 95° C. for 5 minutes, and an aliquot is loaded by electrokinetic injection (30 sec at 1.5 kV) onto a 36 cm long capillary tube loaded with POP6™ (Applied Biosystems) on an ABI Prism 3100 Genetic Analyzer™, 15 kV run voltage, 60° C. for 20 minutes using a FAM™, VIC™ and LIZ™ Matrix (e.g., GENEMAPPER G5 Matrix, Applied Biosystems).

Electrophoretic Analysis:

In the resulting electropherogram, fluorescent peaks are observed for different mobility probes, due to their distinct combinations of mobility and fluorescent label. The mobility and fluorescent signal for each mobility probe is usually already known from prior experimentation, so that the corresponding target sequences can be readily identified. In some embodiments, two different mobility probes may migrate with the same mobility, but they can be distinguished if they comprise different labels (e.g., FAM and VIC). In some embodiments, each mobility probe is designed to migrate with a distinct mobility, and the attached fluorescent label alternates between FAM and VIC for each successive peak, to further simplify identification of the probes. A size standard can also be used to facilitate identification of the probes.

Additional guidance for performing examples consistent with the present teachings can be found in the SNPlex User Manual, available from Applied Biosystems, as well as routine molecular biology treatises such as Sambrook and Russell, Molecular Cloning $3^{rd}$ Edition.

All of the foregoing cited references are expressly incorporated by reference. Recognizing the difficulty of ipsissima verba in multiple documents related to the complex technology of molecular biology, it will be appreciated that when deviances in the nature of a definition are encountered, the definitions provided in the instant application will control.

The invention claimed is:

1. A method of forming a concatameric ligation product comprising;
providing a target polynucleotide, a primary looped linker, a primary oligonucleotide, a secondary oligonucleotide, and a secondary looped linker;
performing, in any suitable order:
hybridizing the primary oligonucleotide and the secondary oligonucleotide to the target polynucleotide;
hybridizing the primary looped linker to the primary oligonucleotide;
hybridizing the secondary looped linker to the secondary oligonucleotide;
ligating the primary looped linker to the primary oligonucleotide;
ligating the primary oligonucleotide to the secondary oligonucleotide; and,
ligating the secondary oligonucleotide to the secondary looped linker; and,
forming a concatameric ligation product.

2. A method of forming a nuclease-resistant ligation product comprising;
providing a target polynucleotide, a primary looped linker, a primary oligonucleotide, a secondary oligonucleotide, and a secondary looped linker,
wherein the primary looped linker comprises a blocking moiety, the secondary looped linker comprise a blocking moiety, or the primary looped linker comprises a blocking moiety and the secondary looped linker comprises a blocking moiety;
performing, in any suitable order;
hybridizing the primary oligonucleotide and the secondary oligonucleotide to the target polynucleotide;
hybridizing the primary looped linker to the primary oligonucleotide;
hybridizing the secondary looped linker to the secondary oligonucleotide;
ligating the primary looped linker to the primary oligonucleotide;
ligating the primary oligonucleotide to the secondary oligonucleotide; and,
ligating the secondary oligonucleotide to the secondary looped linker; thereby
forming a nuclease-resistant ligation product; and,
optionally treating the nuclease-resistant ligation product with at least one nuclease wherein the nuclease resistant ligation product internal to the blocking moiety(s) is not degraded by the nuclease.

3. A method of determining a target polynucleotide comprising;
forming a concacatmeric ligation product according to the method of claim 1, wherein the concatameric ligation product comprises a primary looped linker, a primary oligonucleotide, a secondary oligonucleotide, and a secondary looped linker;
measuring the concatameric ligation product; and,
determining the target polynucleotide.

4. A method of determining an allele at a single nucleotide polymorphism (SNP) locus comprising;
forming a concatameric ligation product according to the method of claim 1, wherein the concatameric ligation product comprises a primary looped linker, a primary oligonucleotide, a secondary oligonucleotide, and a secondary looped linker, wherein the primary oligonucleotide comprises a 3' discriminating nucleotide,
measuring the concatameric ligation product; and,
determining the identity of the allele at the SNP locus.

5. The method according to claim 4 wherein determining the concatameric ligation product comprises;
hybridizing a mobility probe to an amplified concatameric ligation product and eluting the hybridized mobility probe; and,
measuring the eluted mobility probe with a mobility dependent analysis technique.

6. The method according to claim 5 wherein the mobility dependent analysis technique is capillary electrophoresis.

* * * * *

UNITED STATES PATENT AND TRADEMARK OFFICE
CERTIFICATE OF CORRECTION

PATENT NO. : 7,208,278 B2 Page 1 of 1
APPLICATION NO. : 10/982619
DATED : April 24, 2007
INVENTOR(S) : Caifu Chen et al.

It is certified that error appears in the above-identified patent and that said Letters Patent is hereby corrected as shown below:

Claim 3, Column 38, line 12, please replace "concacatmeric" with --concatameric--.

Signed and Sealed this

Thirtieth Day of September, 2008

JON W. DUDAS
*Director of the United States Patent and Trademark Office*